US008389803B2

(12) United States Patent
Jeon et al.

(10) Patent No.: US 8,389,803 B2
(45) Date of Patent: Mar. 5, 2013

(54) **GENES FOR ENHANCING RESISTANCE TO *MAGNAPORTHE ORYZAE* AND USES THEREOF**

(75) Inventors: Jong Seong Jeon, Anyang-si (KR); Pamela Ronald, Davis, CA (US); Young Su Seo, Busan (KR); Sang Kyu Lee, Yongin-si (KR); Min Young Song, Suwon-si (KR); Hye Kyung, Suwon-si (KR); Se Ho Ko, Suwon-si (KR); Jung Pil Suh, Suwon-si (KR); Gi Hwan Yi, Daegu (KR); Gyn Heung An, Pohang-si (KR); Tae Ryoung Hahn, Yongin-si (KR); Jae Hwan Roh, Suwon-si (KR); Peijian Cao, Hangzhou (CN)

(73) Assignees: University-Industry Cooperation Group of Kyung Hee University, Yongin-Si, Gyeonggi-Do (KR); The Regents of The University of California, Oakland, CA (US)

( * ) Notice: Subject to any disclaimer, the term of this patent is extended or adjusted under 35 U.S.C. 154(b) by 238 days.

(21) Appl. No.: 12/733,058

(22) PCT Filed: Jul. 15, 2009

(86) PCT No.: PCT/KR2009/003898
§ 371 (c)(1), (2), (4) Date: Jul. 6, 2010

(87) PCT Pub. No.: WO2010/008204
PCT Pub. Date: Jan. 21, 2010

(65) Prior Publication Data

US 2010/0287664 A1 Nov. 11, 2010

(30) Foreign Application Priority Data

Jul. 18, 2008 (KR) ........................ 10-2008-0069820

(51) Int. Cl.
*A01H 5/00* (2006.01)
*C12N 15/09* (2006.01)
*C12N 15/29* (2006.01)
*C12N 15/82* (2006.01)

(52) U.S. Cl. ... 800/279; 536/23.6; 536/23.1; 435/320.1; 435/468; 435/419; 800/278; 800/320; 800/317; 800/298; 800/295

(58) Field of Classification Search ........................ None
See application file for complete search history.

(56) References Cited

U.S. PATENT DOCUMENTS 4,940,838 A 7/1990 Schilperoort et al.

FOREIGN PATENT DOCUMENTS

EP 0 116 718 A1 8/1984
EP 0 120 516 A2 10/1984
EP 0 301 316 A2 2/1989
KR 10-0701302 A 4/2006
KR 10-0764563 A 9/2006

OTHER PUBLICATIONS

GenBank Accession No. AF294978, "Cloning vector pC1300intC, complete sequence"; submitted Aug. 11, 2000, Dept. of Molecular Cell Biology, Institute for Molecular Plant Sciences; 4 pages.

GenBank Accession No. EU869185, "Oryza sativa Japonica Group Pi5-1 (Pi5-1) gene, complete cds"; submitted Jul. 3, 2008, Graduate School of Biotechnology, Kyung Hee University; 4 pages.

GenBank Accession No. EU869186, "Oryza sativa Japonica Group Pi5-2 (Pi5-2) gene, complete cds"; submitted Jul. 3, 2008, Graduate School of Biotechnology, Kyung Hee University; 4 pages.

Hammond-Kosac, Kim E., et al., "Plant Disease Resistance Genes"; Annu. Rev. Plant Physiol. Plant Mol. Biol. 1997, 48: pp. 575-607.

Van Der Biezen and Jones, "Plant disease-resistance proteins and the gene-for-gene concept"; TIBS (Trends Biochem. Sci.) 23:, Dec. 1998; pp. 454-456.

Ballini, elsa, et al., "A Genome-Wide Meta-Analysis of Rice Blast Resistance Genes and Quantitative Trait Loci Provides New Insights into Partial and Complete Resistance"; The American Phytopathological Society, Mol. Plant Microbe Interact (IPMI) vol. 21, No. 7, 2008; pp. 859-868.

Wang, Zi-Xuan, et al., "The Pib gene for rice blast resistance belongs to the nucleotide binding and leucine-rich repeat class of plant disease resistance genes"; The Plant Journal (1999) 19(1); pp. 55-64.

Wang, Guo-Liang, et al., "RFLP Mapping of Genes Conferring Complete and Partial Resistance to Blast in a Durably Resistant Rice Cultivar"; Genetics 136: (Apr. 1994); pp. 1421-1434.

Jeon, J.-S., et al., "Genetic and physical mapping of Pi5(t), a locus associated with broad-spectrum resistance to rice blast"; Mol Gen Genomics (2003) 269: pp. 280-289.

Krens, F. A., et al., "In vitro transformation of plant protoplasts with Ti-plasmid DNA"; Nature vol. 296; Mar. 4, 1982; 72-74.

Negrutiu, I., et al., "Hybrid genes in the analysis of transformation conditions, I. Setting up a simple method for direct gene transfer in plant protoplasts"; Plant Molecular Biology 8; (1987); pp. 363-373.

Shillito, R. D., et al., "High Efficiency Direct Gene Transfer to Plants"; Bio/Technology, vol. 3, Dec. 1985; pp. 1099-1102.

Crossway, Anne, et al., "Integration of foreign DNA following microinjection of tobacco mesophyll protoplasts"; Mol Gen Genet (1986) 202:; pp. 179-185.

(Continued)

*Primary Examiner* — Medina A Ibrahim
(74) *Attorney, Agent, or Firm* — Osha Liang LLP

(57) ABSTRACT

The present invention relates to Pi5-1 and Pi5-2 proteins which enhance resistance to *Mag-naporthe oryzae*, genes which encode the proteins, a recombinant vector comprising the genes, a plant transformed with the recombinant vector and seeds thereof, a method of increasing resistance to a plant pathogen by expressing the genes in a plant, antibodies against the proteins, and a composition comprising the genes which are useful for enhancing resistance to a plant pathogen.

10 Claims, 7 Drawing Sheets

OTHER PUBLICATIONS

Klein, T. M., et al., "High-velocity microprojectiles for delivering nucleic acids into living cells"; Nature vol. 327, May 7, 1987; pp. 70-73.

Liu, G., et al., "Two broad-spectrum blast resistance genes, Pi9(t) and Pi2(t), are physically linked on rice chromosome 6"; Mol Genet Genomics (2002) 267:; pp. 472-480.

Chen, D.-H., et al., "A Rapid DNA Minipreparation Method Suitable for AFLP and Other PCR Applications"; Plant Molecular Biology Reporter 17:, 1999; pp. 53-57.

Jeon, Jong-Seong, et al., "T-DNA insertional mutagenesis for functional genomics in rice"; The Plant Journal (2000) 22(6); pp. 561-570.

Sinapidou, Eva, et al., "Two TIR:NB:LRR genes are required to specify resistance to *Peronospora parasitica* isolate Cala2 in Arabidopsis"; The Plant Journal (2004) 38; pp. 898-909.

1
MVGAEMLVAAAVSQVARKINDIVGVAQGEV*KLCCNFSDDLEGIKDTLVYLETLLKNAENNSFGSDRA*NLRHWLGQ
IKSLAYDIEDIVDGYYSSKEQFDGGSYAQKGSL

NB

109
FCSLSNPMLLKGSMVYKMKSKREMLQQSQQLPNQYHFLSYINSAVHYFEEKQTTSYRNTDIAIVGRDADLDHLMD

P-loop
LLMQNSAEELCIIPIVGPVGFGKTSLAQLVFNDTRTEVFSFRIWVHVSMGNINLEKIGRDIVSQTTEKIEGNMQL kinase-2 RNBS-B
QSIKNAVQRVLNKYSCLIIIDSLWGKDEEVNELKQMLLTGRHTESKIIVTTHSNKVAKLISTVPLYKLAALSEDD GLPL
CLKIFSQRAMTGPGDPLFREYGEEIVRRCEGTPLVANFLGSVVNAQRQRREIWQAAKDEEMWKIEEDYPQDKISP RNBS-D
LFPSFKIIYYNMPHELRLCFVYCSIFPKGTVIEKKKLIQQWIALDMIESKHGTLPLDVTAEKYIDELKAIYFLQV MHDV
LERSQNDAERSSASEEMLRMHNLAHDLARSVAGEDILVILDAENERNARYCNYRYAQVSASSLESIDRKAWPSKA
RSLIFKNSGVDFEHVSEV

LRR

577
LSVNKYLRVLDLSGCCVQDIPSP
IFQLKQLRYLDVSSLSITALPLQ
ISSFHKLQMLDLSETELTELPPFISN
LKGLNYLNLQGCQKLQRLNSLHL
LHDLHYLNLSCCPEVTSFPESIEN
LTKLRFLNLSGCSKLSTLPIRFLESFAS
LCSLVDLNLSGFEFQMLPDFFGN
IYSLQYLNLSKCLKLEVLPQSFGQ
LAYLKSLNLSYCSDLKLLESFEC
LTSLRFLNLSNCSRLEYLPSCFDK
LNNLESLNLSQCLGLKALPES
LQNLKNLQLDVSGCQDCIVQSFSLST

CT

865
RSSQSCQRSEKAEQVRSRNSEISEITYEEPAEIELLKNNPSKDLASISHLNEDRIEEPEVVTEPSATRGMVQQIP
GNQLSSPSSHLSSFASSSAPFASSSSDTSTSEHPVPNEEAAALTVPRSKEKCDNTPMPVKDGLISEDDAPVHLHQ
KPLQATAMAAI

Fig. 6

```
1                                                                                    CC
MATAGAAVDRLLRRLASGAGRLELPSSIDEDMAHVKRTLARLQDVLLTVEGKYFKMGAEVQEWMRKIKQIAYGIQ
DLLDEFEDSSGTGSQRNGSRISEGTLSCSSAPF

109                                                                                  NB
FCHLSRSQRIRVLKRKLDQSTKDTSVFSLLQHSLSNLDKSNEQEVLLHRTEIIGRDTDKENIKNLLLQNDVDKLP
             P-loop
IIPIVGLAGLGKTAVAKLIFHEQGEGWNFDQRIWVHLDKKLDLNKIANSIISQVNQSVDTTKNQIQNNLQFKRNC
              kinase-2                      RNBS-B
LQEVLCDQSSLIVLDDLFSTEENQIAELKEMLRGTKKGTKIIVTTSSEISAELIHTVPPYKLGPLSEGDCSTIFC
                                   GLPL
QRAFGDGHENSSLTEIAKQIVKRCEGIPAVAYSLGSLVRNKNKEAWLYARDKEIWELPTLFPNGFELLASFSEMY
                                RNBS-D
ICMPSALKSCFAYLSTIPKGTIIDREKLIEQWIALDMVGSKHGTLPAYVQGEMFIQQLLSISFLQVRNKPSATRI
                    MHDV
RDTNQSKELRIHNLVHDFAMYVARDDLIILDGGEKASSLRKNIHVFYGVVNNDIGQSALRKGLLSSARAVHFKNC
KSEKLLVEA

568                                                                                  LRR
FSVLNHLRVLDLSGCCIVELPDF
ITNLRHLRYLDVSYSRILSLSTQ
LTSLSNLEVLDLSETSLELLPSSIGS
FEKLKYLNLQGCDKLVNLPPFVCD
LKRLENLNLSYCYGITMLPPN
LWKLHELRILDLSSCTDLQEMPYL
FGNLASLENLNMSKCSKLEQLPES
LGDLCYLRSFNLSGCSGLKMLPESLKN
LTNLEYINLSNIGESIDFNQ
IQQLRHILKKTFFSGDIGGSELQ

803                                                                                  CT
TCEHAADSADSKKEITMDFSANLHGNITLPPKCSTEEKSGENSERFLSAAVREDSSSTDVSTYVKPVVSSLIGVL
RRPTRLDVPAGAMASQVGLAQMPSSNNGKAGPHPTMAAAQTPEIDQPVHKRVRWDDIIDYSRPPNSKPARSASLV
QSTDLSTPKKSYKKIHSMPVVYSSIPKGSSGGTYLMPAKAIASSYRRYSPQRWEQHIGYQGTDEDELMVVPPFGE
WDQSPTLRKSDFRYEKVFAKLTEEKMSGQRQKPQQV
```

GENES FOR ENHANCING RESISTANCE TO *MAGNAPORTHE ORYZAE* AND USES THEREOF

TECHNICAL FIELD

The present invention relates to genes for enhancing resistance to *Magnaporthe oryzae* and use thereof. More specifically, the present invention relates to Pi5-1 and Pi5-2 proteins which enhance resistance to *Magnaporthe oryzae*, genes which encode the proteins, a recombinant vector comprising the genes, a plant transformed with the recombinant vector and seeds thereof, a method of increasing resistance to a plant pathogen by expressing the genes in a plant, antibodies against the proteins, and a composition comprising the genes which are useful for enhancing resistance to a plant pathogen.

BACKGROUND ART

The innate immune response is critical to the survival of plants and animals. The response is mediated by the detection of pathogen-associated molecular patterns (PAMPs) (also referred to as microbe-associated molecular patterns) or avirulence (Avr) proteins by pathogen recognition receptors (PRRs; also called pattern recognition receptors or disease resistance proteins). In animals, a family of cytosolic PRRs that contain a nucleotide-binding oligomerization domain (NOD) mediates the apoptotic and inflammatory responses critical to protection from pathogen invasion. Plants also contain a set of intracellular PRR proteins, called NB-LRR (nucleotide binding-leucine rich repeat) R proteins, which are structurally similar to animal NOD proteins. These plant NB-LRR proteins are characterized by a tripartite domain architecture consisting of an N-terminal coiled-coil (CC) or Toll/interleukin-1 receptor (TIR) domain, a central NB domain, and a C-terminal LRR domain (Hammond-Kosack and Jones (1997) Annu. Rev. Plant Physiol. Plant Mol. Biol. 48: 575-607) and typically recognize pathogen-derived Avr proteins (also called effectors) (Van der Biezen and Jones (1998) Trends Biochem. Sci. 23: 454-456).

Rice blast is one of the most devastating diseases of rice and occurs in all areas of the world where rice is cultivated. More than 70 blast R genes that confer resistance to geographically different sets of the rice blast pathogen *Magnaporthe oryzae* isolates have been identified to date (Ballini et al. (2008) Mol. Plant. Microbe Interact. 21: 859-868). For example, Pib confers robust resistance to a majority of the Japanese *Magnaporthe oryzae* isolates (Wang et al. (1999) Plant J. 19: 55-64). In contrast, Pi37 confers only partial resistance to Japanese isolates but complete resistance to Chinese isolates of the same pathogen. Hence, the isolation of multiple R genes is required to fully understand the molecular basis of the resistance to rice blast. Such characterization of these genes will facilitate development of agronomically useful rice cultivars through markerassisted breeding or through transgenic approaches.

To date, a total of nine rice blast resistance genes have been cloned and characterized: Pib, Pita, Pi9, Pi2 and Piz-t, Pi-d2, Pi36, Pi37, and Pikm. With the exception of Pi-d2, a non-RD receptor-like kinase, these genes all encode NB-LRR type proteins. Distinct features of these cloned rice blast resistance genes have been observed. The Pib protein contains a duplicated NB region. Pita lacks a classic LRR but contains a leucine-rich domain (LRD) consisting of imperfect repeats of various lengths. A single amino acid difference at the Pita LRD was found to distinguish resistant from susceptible alleles. The allelic genes Pi2 and Piz-t show 8 amino acid differences within three consecutive LRRs, and these residues are responsible for resistance specificity. The Pi9 gene strongly resembles the Pi2 and Piz-t genes and is located within the same region on chromosome 6. The Pikm-mediated resistance requires two adjacent NB-LRR genes Pikm1-TS and Pikm2-TS. Among these cloned R genes, only Pita has been observed to interact with the corresponding *Magnaporthe oryzae* avirulence protein, AvrPita. Thus, defense signaling mediated by NB-LRR type proteins remains poorly characterized in rice.

It has been reported that Pi5 confers resistance to many *Magnaporthe oryzae* isolates collected from Korea and the Philippines (Wang et al. (1994) Genetics 136: 1421-1434). To gain a further understanding of the molecular basis of Pi5-mediated rice blast resistance, we used a map-based method to isolate the Pi5 genomic region. We previously mapped Pi5 to a 170-kb interval on the short arm of chromosome 9 in the RIL260 rice cultivar (Jeon et al. (2003) *Molecular Genetics and Genomics* 269: 280-289).

According to Korean Patent Registration No. 10-0764563, a gene for inducing resistance to a plant disease, a vector comprising the gene and a transformant obtained from the vector are described. Furthermore, according to Korean Patent Registration No. 10-0701302, plant disease-resistant ogpr 1 gene separated from wild rice, the amino acid sequence of the gene, and a transformant using the same are described. However, said gene is different from the gene of the present invention.

DISCLOSURE OF INVENTION

Technical Problem

The present invention is devised in view of the above-described needs. Specifically, in order to further narrow Pi5 resistant gene locus based on a new mapping population, two types of CC-NB-LRR genes, which are candidate genes for Pi5, were identified by sequence analysis of the genomic region having resistance. In addition, transgenic rice plants expressing one or both of said candidate genes were produced and their phenotypes resistant to *Magnaporthe oryzae* were characterized.

Technical Solution

In order to solve the problems described above, the present invention provides Pi5-1 and Pi5-2 proteins which enhance resistance to *Magnaporthe oryzae*.

Further, the present invention provides genes which encode the proteins.

Further, the present invention provides a recombinant vector comprising the genes.

Further, the present invention provides a plant transformed with the recombinant vector and seeds thereof.

Further, the present invention provides a method of increasing resistance to a plant pathogen by expressing the genes in a plant.

Further, the present invention provides antibodies against the proteins.

Still further, the present invention provides a composition comprising the genes which are useful for enhancing resistance to a plant pathogen.

Advantageous Effects

According to the present invention, based on coordination between the Pi5-1 gene and the Pi5-2 gene, resistance to a plant pathogen, in particular *Magnaporthe oryzae*, can be enhanced.

BRIEF DESCRIPTION OF DRAWINGS

FIGS. 5 and 6 represent amino acid sequences of Pi5-1 protein (SEQ ID NO: 1) and Pi5-2 protein(SEQ ID NO: 2), respectively. Both resistance proteins contain a coiled-coil (CC), nucleotide-binding site (NB), leucine-rich repeat (LRR), and C-terminal region (CT). Amino acids 31-67 of Pi5-1 SEQ ID NO: 1) and 26-87 of Pi5-2 (SEQ ID NO: 2), shown in underlined italics, contain CC motifs. The conserved internal motifs characteristic of NB proteins, namely the P-loop, kinase-2, RNBS-B, GLPL, RNBS-D, and MHDV domains, are underlined and in bold. A conserved xLDL motif found in the LRR of many NB-LRR proteins is also underlined.

MODE FOR THE INVENTION

Figure 1:
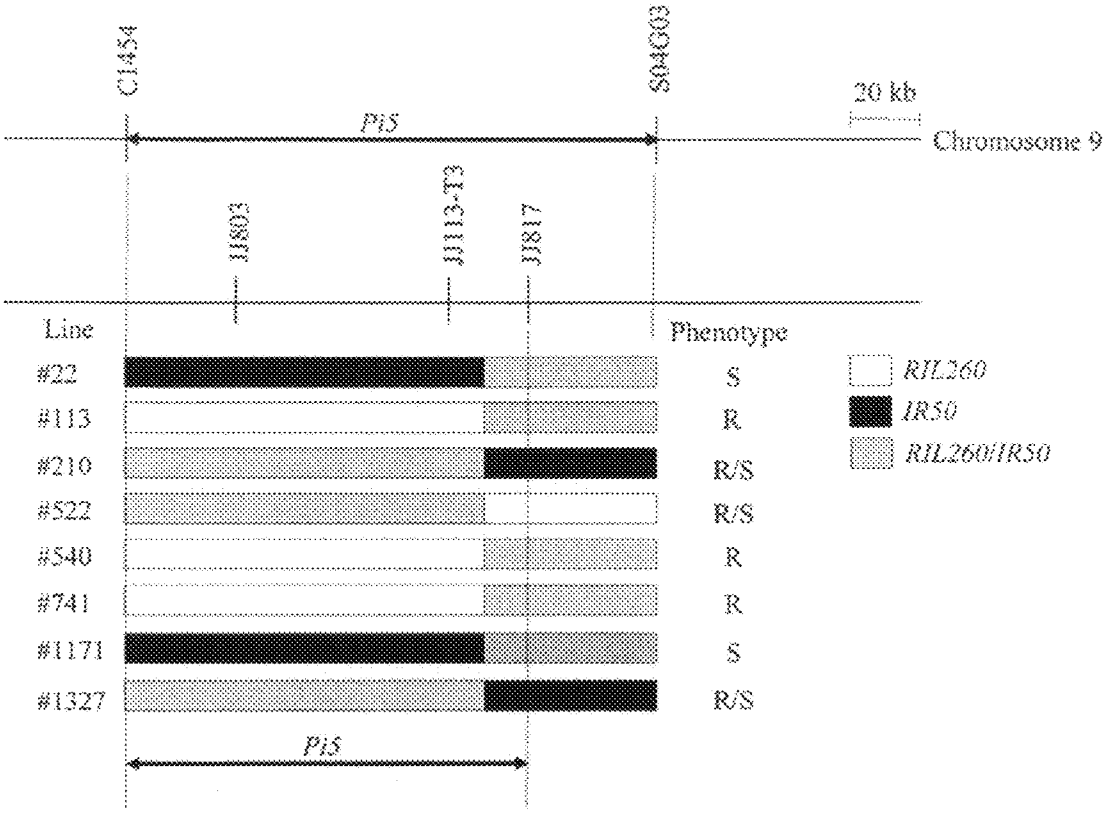
FIG. 1 represents chromosomal location of the Pi5 locus in the RIL260/IR50 population. (top) The 170-kb Pi5 resistance genomic region is shown between the markers C1454 and S04G03 in RIL260/CO39 and RIL260/M202. (bottom) A schematic diagram of the 8 rare recombinants in the Pi5 region identified in the RIL260/IR50 population. Breakage points are indicated between the relevant molecular markers. Open bars indicate the presumed RIL260 genome, black bars indicate the IR50 genome, and shaded bars indicate that the region is heterozygous between the two genomes. The bold arrow indicates the 130-kb minimal interval carrying the Pi5 locus, delimited by analysis of the mapping population. Resistance to *Magnaporthe* oryzae PO6-6 were determined in the $F_3$ progeny of each line. R, resistant; S, susceptible; R/S, segregating line.

In order to achieve the purpose of the invention as described above, the present invention provides Pi5-1 and Pi5-2 proteins which can enhance resistance to *Magnaporthe oryzae*. In this regard, each of the Pi5-1 and Pi5-2 proteins cannot independently enhance resistance to *Magnaporthe oryzae*. Instead, only with coordination between the Pi5-1 and Pi5-2 proteins, enhancement of resistance to *Magnaporthe oryzae* can be obtained.

The scope of the Pi5-1 and Pi5-2 proteins of the present invention includes a protein having an amino acid sequence represented by SEQ ID NO: 1 or SEQ ID NO: 2 that is isolated from rice, and functional equivalents of said proteins. The term "functional equivalent" means that, as a result of addition, substitution or deletion of amino acid residues, it has an amino acid sequence with at least 70%, preferably at least 80%, more preferably at least 90%, still more preferably at least 95% homology with the amino acid sequence that is represented by SEQ ID NO: 1 or SEQ ID NO: 2, thus indicating a protein which has substantially the same physiological activity as the protein expressed by SEQ ID NO: 1 or SEQ ID NO: 2. The term "substantially the same physiological activity" indicates an activity of enhancing resistance of a plant to *Magnaporthe oryzae.*

The present invention further provides genes which encode said Pi5-1 and Pi5-2 proteins. Each of the Pi5-1 and Pi5-2 genes of the present invention may also comprise a coiled-coil (CC), a nucleotide-binding (NB) domain and a leucine-rich repeat (LRR) domain (see FIG. 5 and FIG. 6). The genes of the present invention include both genomic DNA and cDNA which encode Pi5-1 and Pi5-2 proteins. Specifically, cDNA sequence of Pi5-1 includes 5' and 3' non-translated regions, each comprising 70 by and 220 bp, respectively, and encodes 1,025 amino acids. cDNA sequence of Pi5-2 includes 5' and 3' non-translated regions, each comprising 73 by and 164 bp, respectively, and encodes 1,063 amino acids.

Preferably, each of the genomic DNAs of Pi5-1 and Pi5-2 of the present invention may comprise a nucleotide sequence that is described either by SEQ ID NO: 3 or by SEQ ID NO: 4. Further, each of the cDNAs of Pi5-1 and Pi5-2 of the present invention may comprise a nucleotide sequence that is described either by SEQ ID NO: 5 or by SEQ ID NO: 6. Variants of said nucleotide sequence are also within the scope of the present invention. Specifically, said gene may comprise a nucleotide sequence with at least 70%, preferably at least 80%, more preferably at least 90%, still more preferably at least 95% homology with the nucleotide sequences of SEQ ID NO: 3 to SEQ ID NO: 6. The "sequence homology %" for a certain polynucleotide is determined by comparing two nucleotide sequences that are optimally arranged with a region to be compared. In this regard, a part of the polynucleotide sequence in a region to be compared may comprise an addition or a deletion (i.e., a gap) compared to a reference sequence (without any addition or deletion) relative to the optimized arrangement of the two sequences.

Further, the present invention provides a recombinant vector comprising the Pi5-1 and Pi5-2 of the present invention.

The term "recombinant" indicates a cell which replicates a heterogeneous nucleotide or expresses said nucleotide, a peptide, a heterogeneous peptide, or a protein encoded by a heterogeneous nucleotide. Recombinant cell can express a gene or a gene fragment in a form of a sense or antisense, that are not found in natural state of cell. In addition, a recombinant cell can express a gene that is found in natural state, provided that said gene is modified and re-introduced into the cell by an artificial means.

The term "vector" is used herein to refer DNA fragment (s) and nucleotide molecules that are delivered to a cell. Vector can replicate DNA and be independently reproduced in a host cell. The terms "delivery system" and "vector" are often interchangeably used. The term "expression vector" means a recombinant DNA molecule comprising a desired coding sequence and other appropriate nucleotide sequences that are essential for the expression of the operatively-linked coding sequence in a specific host organism.

Preferably, the recombinant vector of the present invention is a recombinant plant expression vector.

A preferred example of plant expression vector is Ti-plasmid vector which can transfer a part of itself, i.e., so-called T-region, to a plant cell when the vector is present in an appropriate host such as *Agrobacterium tumefaciens*. Other types of Ti-plasmid vector (see EP 0 116 718 B 1) are currently used for transferring a hybrid gene to protoplasts that can produce a new plant by appropriately inserting hybrid DNA to a plant genome. Especially preferred form of Ti-plasmid vector is a so-called binary vector which has been disclosed in EP 0 120 516 B1 and U.S. Pat. No. 4,940,838. Other vector that can be used for introducing the DNA of the present invention to a host plant can be selected from a double-stranded plant virus (e.g., CaMV), a single-stranded plant virus, and a viral vector which can be originated from Gemini virus, etc., for example a non-complete plant viral vector. Use of said vector can be advantageous especially when a plant host cannot be appropriately transformed.

Expression vector would comprise at least one selective marker. Said selective marker is a nucleotide sequence having a property which allows a selection based on a common chemical method. Any kind of gene that can be used for the differentiation of transformed cells from non-transformed cell can be a selective marker. Example includes, a gene resistant to herbicide such as glyphosate and phosphintricin, and a gene resistant to antibiotics such as kanamycin, G418, bleomycin, hygromycin, and chloramphenicol, but not limited thereto.

For the plant expression vector according to one embodiment of the present invention, a promoter can be any of CaMV 35S, actin, ubiquitin, pEMU, MAS or histone promoter, but not limited thereto. The term "promoter" means a DNA molecule to which RNA polymerase binds in order to initiate its transcription and it corresponds to a DNA region upstream of a structural gene. The term "plant promoter" indicates a promoter which can initiate transcription in a plant cell. The term "constitutive promoter" indicates a promoter which is active in most of environmental conditions and development states or cell differentiation states. Since a transformant can be selected with various mechanisms at various stages, a constitutive promoter can be preferable for the present invention. Therefore, a possibility for choosing a constitutive promoter is not limited in the present invention.

For the above-described terminator, any conventional terminator can be used for the present invention. Example includes, nopaline synthase (NOS), rice α-amylase RAmy1 A terminator, phaseoline terminator, and a terminator for optopine gene of *Agrobacterium tumefaciens*, etc., but are not limited thereto. Regarding the necessity of terminator, it is generally known that such region can increase a reliability and an efficiency of transcription in plant cells. Therefore, the use of terminator is highly preferable in view of the contexts of the present invention.

Further, the present invention provides a plant that is transformed with the recombinant vector according to the present invention.

The plant according to the present invention is preferably a monocot plant including rice, barley, maize, wheat, rye, oat, turf grass, hay, millet, sugar cane, rye grass, orchard grass, and the like. Most preferably, it is rice.

Further, the present invention provides seeds of the above-described plants. Preferably, the seeds are rice seeds.

Further, the present invention provides a method of increasing resistance to a plant pathogen, comprising steps of transforming a plant with the recombinant vector of the present invention which includes the Pi5-1 and Pi5-2 genes and then expressing the Pi5-1 and Pi5-2 genes in the plant. Preferably, the pathogen is *Magnaporthe oryzae*. The above-described plant is preferably a monocot plant including rice, barley, maize, wheat, rye, oat, turf grass, hay, millet, sugar cane, rye grass, orchard grass, and the like. Most preferably, it is rice.

Plant transformation means any method by which DNA is delivered to a plant. Such transformation method does not necessarily have a period for regeneration and/or tissue culture. Transformation of plant species is now quite general not only for dicot plants but also for monocot plants. In principle, any transformation method can be used for introducing a hybrid DNA of the present invention to an appropriate progenitor cells. It can be appropriately selected from a calcium/polyethylene glycol method for protoplasts (Krens, F. A. et al., 1982, Nature 296, 72-74; Negrutiu I. et al., June 1987, Plant Mol. Biol. 8, 363-373), an electroporation method for protoplasts (Shillito R. D. et al., 1985 Bio/Technol. 3, 1099-1102), a microscopic injection method for plant components (Crossway A. et al., 1986, Mol. Gen. Genet. 202, 179-185), a particle bombardment method for various plants components (DNA or RNA-coated) (Klein T. M. et al., 1987, Nature 327, 70), or a (non-complete) viral infection method in *Agrobacterium tumefaciens* mediated gene transfer by plant invasion or transformation of fully ripened pollen or microspore (EP 0 301 316), etc. A method preferred in the present invention includes *Agrobacterium* mediated DNA transfer. In particular, so-called binary vector technique as disclosed in EP A 120 516 and U.S. Pat. No. 4,940,838 can be preferably adopted for the present invention.

The term "plant cell" that is used for the plant transformation according to the present invention can be any plant cell. The plant cell can be a cultured cell, a cultured tissue, a cultured organ, or a whole plant, preferably a cultured cell, a cultured tissue or a cultured organ, and more preferably any form of a cultured cell. Preferably, the plant is rice.

The term "plant tissue" includes either differentiated or undifferentiated plant tissue, including root, stem, leaf, pollen, seed, cancerous tissue and cells having various shape that are used for culture, i.e., single cell, protoplast, bud and callus tissue, but not limited thereto. Plant tissue can be in planta or in a state of organ culture, tissue culture or cell culture.

Further, the present invention provides antibodies against the Pi5-1 and Pi5-2 proteins of the present invention. According to the present invention, the term "antibody" includes a monoclonal antibody, a multi-specific antibody, a human antibody, a humanized antibody, a camelised antibody, a chimera antibody, a single-chain Fvs (scFv), a single-chain antibody, a single-domain antibody, a Fab fragment, a F(ab) fragment, a disulfide-bonding Fvs (sdFv), an anti-idiotype (anti-Id) antibody, or a fragment which binds to any of the above-described epitopes. In particular, an immunoglobulin molecule and an immunologically-active fragment of an immunoglobulin molecule, i.e., a molecule which comprises an antigen-binding region, are included in the antibody of the present invention. An immunoglobulin molecule can be any kind including IgG, IgE, IgM, IgD, IgA, and IgY or any class including $IgG_1$, $IgG_2$, $IgG_3$, $IgG_4$, $IgA_1$, and $IgA_2$ or their subclass.

The antibody of the present invention can be prepared according to a general method which comprises steps of cloning the genes of the present invention in an expression vector by following a typical procedure to obtain a protein and preparing the antibody from the protein. Herein, a partial peptide which can be generated from the protein is also included. As for a partial peptide of the present invention, it comprises at least seven amino acids, preferably at least nine amino acids, and more preferably at least twelve amino acids. Type of the antibody of the present invention is not specifically limited. A monoclonal antibody, a polyclonal antibody and a part of such antibodies having an antigen-binding property are all included in the antibody of the present invention. All kinds of immunoglobulin antibody are also included. Furthermore, a special antibody such as a humanized antibody and the like is also included in the antibody of the present invention.

Still further, the present invention provides a composition comprising the Pi5-1 and Pi5-2 genes for enhancing resistance to a plant pathogen. Since the Pi5-1 and Pi5-2 proteins of the present invention enhance resistance to a plant pathogen based on coordination between them, the composition comprising the Pi5-1 and Pi5-2 genes can be used for enhancing resistance to a plant pathogen. Preferably, the plant pathogen is *Magnaporthe oryzae.*

The present invention will now be described in greater detail with reference to the following examples. However, it is only to specifically exemplify the present invention and in no case the scope of the present invention is limited by these examples.

EXAMPLES

Plant Materials

The RIL260 rice cultivar carrying the Pi5 allele and a rice blast-susceptible cultivar, IR50, were used as the parental lines in this study. The RIL260 and IR50 cultivars were crossed to generate a mapping population for genetic linkage analysis. Self-pollinated seeds ($F_2$) of the RIL260/IR50 $F_1$ individuals were collected to obtain a sufficiently large mapping population. A japonica rice cultivar, Dongjin, was used as the susceptible control in the *Magnaporthe oryzae* inoculation and rice transformation experiments. RIL260 and the monogenic rice line IRBL5-M carrying Pi5 were used as the resistant control cultivars in the *Magnaporthe oryzae* inoculation experiments. An additional 8 monogenic rice lines, IRBL1-F5, IRBL9-W, IRBLb-B, IRBLta-K1, IRBLz-Fu, IRBLks-F5, IRBLkm-Ts, and IRBLsh-S, and the susceptible background cultivar of these monogenic lines, Lijiangxintuanheigu (LTH) were also used in the inoculation experiments to determine the virulence pattern of *Magnaporthe oryzae* isolates. Rice seedlings were grown in a greenhouse at 30° C. during the day and at 20° C. at night in a light/dark cycle of 14/10 hr.

Pathogen Inoculation and Disease Evaluation

Magnaporthe oryzae PO6-6, a Philippine isolate, which is incompatible with the Pi5 resistance locus, has been commonly used to detect this locus. To analyze blast resistance in Pi5 transgenic rice plants, an additional 5 different Korean *Magnaporthe oryzae* isolates, KJ105a, KJ107, KJ401, KI215, and R01-1, were used. All inoculations and disease evaluations were conducted in the greenhouse facilities at Kyung Hee University using a method that was slightly modified from Liu et al. (2002, Mol. Genet. Genomics 267: 472-480). Three week-old plants of the $F_3$ progeny of each of the identified recombinant lines and transgenic plants were used in the inoculation experiments. *Magnaporthe oryzae* was grown on oatmeal agar medium for 2 weeks at 24° C. in the dark. Conidia were induced 4 days prior to collection by scratching the plate surface with a sterilized loop. The inoculated plants were placed in sealed containers to maintain humidity at 24° C. in darkness for 24 hr, and then transferred to a growth chamber at 24° C. and 80% humidity under a 14/10-hr (light/dark) photoperiod. Disease evaluation was carried out 7 days after inoculation.

Genotypic Analysis of Progeny from the RIL260/IR50 Mapping Population

Cleaved amplified polymorphic sequence (CAPS) markers for C1454 and JJ817 and a sequence characterized amplified region (SCAR) marker JJ803 (corresponding to the previously reported dominant marker JJ80-T3) were used for the analysis of the RIL260/IR50 segregating progeny (Table 1). The dominant markers JJ113-T3 and S04G03 were additionally utilized as needed.

TABLE 1

PCR primers used in this study

| Marker or gene | Forward primer (5'-3') | Reverse primer (5'-3') |
|---|---|---|
| C1454 | GTATTACCTGAAATCCTA GTGGTG (SEQ ID NO: 7) | AGGAACTACGGTATTACA AGGATC (SEQ ID NO: 8) |
| JJ817 | GATATGGTTGAAAAGCTA ATCTCA (SEQ ID NO: 9) | ATCATTGTCCTTCATATT CAGAGT (SEQ ID NO: 10) |
| JJ803 | AAGTGAGCATCCAGTGCC TAATGA (SEQ ID NO: 11) | AGCCGGTGCTCATAACAC GTATTA (SEQ ID NO: 12) |
| Pi5-1 | TACAAGTTGGCAGCTTTA TCTGAG (SEQ ID NO: 13) | TCAGAAGCACTGGATCTT TCTGCA (SEQ ID NO: 14) |
| Pi5-2 | AGTGAACTCCAAACATGT GAACAC (SEQ ID NO: 15) | TCATACCTGTTGCGGTTT CTGCCT (SEQ ID NO: 16) |
| Actin1 | GGAACTGGATAGGTCAAG GC (SEQ ID NO: 17) | AGTCTCATGGATACCCGC AG (SEQ ID NO: 18) |
| PBZ1 | ACCATCTACACCATGAAG CTTAAC (SEQ ID NO: 19) | GTATTCCTCTTCATCTTA GGCGTA (SEQ ID NO: 20) |

Genomic DNA was isolated from young leaves of rice plants using a simple miniprep method (Chen and Ronald (1999) Plant Mol. Biol. Rep. 17: 53-57). PCR analysis was performed in a final volume of 30 μl (100 pM of each primer, 200 μM each of dNTPs, 10 mM Tris-HCl pH 9.0, 2 mM $MgCl_2$, 50 mM KCl, 0.1% Triton X-100 and 0.5 U Taq polymerase) using 50 ng of genomic DNA as template. PCR products for the CAPS markers C1454 and JJ817 were subsequently digested with Mlu I and AseI, respectively, and then size-fractionated on agarose gels.

DNA Sequencing and Gene Prediction

RIL260 Binary BAC (BIBAC) clones spanning the Pi5 locus were selected for DNA sequencing analysis. Plasmids purified by a minipreparation were partially digested with Sau3AI and separated by agarose gel electrophoresis. The 0.5-3.0 kb genomic DNA fragments were isolated using a commercial kit (Gel Extraction Kit, Qiagen), subcloned into the BamHI site of pBluescriptII SK(−) (Clontech), and then transformed into *E. coli* DH10B by electroporation. For DNA sequencing of each BIBAC clone with a 25-kb average insert size, about 60 clones were selected and sequenced in one or both directions using the T3 and T7 primers.

Similarity searches against the NCBI database (http://www.ncbi.nlm.nih.gov/) were performed using BLAST (Basic Local Alignment Search Tool). To predict proteincoding gene regions, the Rice Genome Automated Annotation System (RiceGAAS) was utilized (http://RiceGAAS.dna.affrc.go.jp/).

Vector Construction for Genetic Complementation Experiments

Genomic DNA regions for Pi5-1 and Pi5-2 were reconstituted by subcloning from BIBAC clones (Jeon et al. (2003) Mol. Genet. Genomics 269: 280-289). To construct a clone carrying the entire Pi5-1 coding region, a 6.6-kb BamHI-SacI fragment of the JJ80 vector that includes the 0.5-kb predicted promoter was subcloned into the binary vector pC1300intC (GenBank accession no. AF294978). The resulting plasmid JJ104 was digested with BamHI and BstEII and fused to 7.3-kb HindIII-BstEII insert of JJ106 to construct JJ105 with a 5.2-kb promoter region. The 0.5-kb SacI-XhoI fragment was amplified by PCR using primers 5'-GTCCAAAGAGAAATGCGACAACAC-3' (SEQ ID NO: 21) and 5'-CGCTCGAGGTGGCATTTCATCCAATAGGCAAC-3' (SEQ ID NO: 22). The resulting product was inserted into the JJ105 to extend the terminator region, yielding the JJ204 construct carrying the 11,516-bp Pi5-1 genomic region.

The Pi5-2 gene was constructed by the multiple ligation of the following four fragments: a 4.2-kb EcoRI-BglII DNA fragment of JJ113, a 200-bp BglII-ClaI PCR product amplified using the primers 5'-GGATGATGTGATCTGCAGAGAAAC-3' (SEQ ID NO: 23) and 5'-CAGCCTCACTGAAATTGCGAAGCA-3' (SEQ ID NO: 24), a 4.2-kb ClaI-XbaI DNA fragment of JJ120, and an EcoRI-XbaI digested pC1300intC vector fragment. In the resulting construct JJ117, the promoter region was extended by cloning the 3.7-kb NsiI-EcoRI fragment of JJ120. Finally, by inserting a 0.9 kb-extended terminator sequence into the Eco065I site of the JJ142 plasmid, the 13,250-bp entire genomic sequence of Pi5-2 in JJ212 was constructed. The cloned genomic sequences in JJ204 and JJ212 were confirmed by DNA sequencing.

Production of Transgenic Rice Plants

Genomic clones for Pi5-1 and Pi5-2 were transformed into *Agrobacterium tumefaciens* EHA105 or LBA4404 by electroporation and introduced into the susceptible rice cultivar Dongjin via *Agrobacterium* mediation according to an established procedure (Jeon et al. (2000) Plant J. 22: 561-570). The transgenic plants ($T_0$) were self-pollinated and $T_1$ seeds were collected. Homozygous Pi5-1 (Pi5-1-63) and Pi5-2 (Pi5-2-74) transgenic lines were then selected from $T_2$ progeny resulting from selfpollination of the $T_1$ lines based on the segregation patterns of the transgenes. $F_1$ plants carrying both Pi5-1 and Pi5-2 were produced from a cross between Pi5-1-63 and Pi5-2-74 lines, and self-pollinated to produce $F_2$ plants.

Isolation of Pi5-1 and Pi5-2 cDNAs

Two preparations of total RNA were prepared from rice leaves collected at 24 and 48 hr after inoculation with *Magnaporthe oryzae* PO6-6 using Trizol reagent (Invitrogen). Purified mRNAs were obtained using the PolyATtract mRNA isolation system (Promega) from each set of total RNA and mixed in a 1:1 ratio for cDNA synthesis. cDNAs larger than 0.5 kb were selected by size fractionation via gel filtration, and a cDNA library was constructed with the Uni-ZAP XR vector (Stratagene). This library was then screened via colony blot hybridizations using probes corresponding to the Pi5-1 and Pi5-2 coding regions, a 570-bp HindIII-KpnI fragment of JJ204 and a 589-bp EcoRV-SpeI fragment of JJ212, respectively. Isolated cDNA clones were analyzed by DNA sequencing.

RT-PCR Analysis

To examine the changes in transcript accumulation in response to pathogen treatment, leaves from each of 10 RIL260, IRBL5-M, and transgenic rice plants inoculated with *Magnaporthe oryzae* PO6-6 were collected at different time periods for RT-PCR analysis. Total RNA was prepared using Trizol reagent and reversetranscribed with an oligo-dT primer and a First Strand cDNA Synthesis Kit (Roche). First-strand cDNA was used in PCR reactions with gene-specific primers. Primers for the rice Actin1 gene and the pathogenesis-related probenazole-inducible (PBZ1) gene were used as internal controls (Table 1). PCR conditions were as follows: 94° C. for 5 min followed by 28-35 cycles of 94° C., 1 min; 56° C., 1 min; and 72° C., 1 min, and a final extension at 72° C. for 5 min. Three independent amplifications were performed for each primer set.

Example 1

Genetic Characterization of a 130-kb Chromosomal Region Carrying Pi5

Previously, the Pi5 resistance gene was delimited to a 170-kb interval between the two flanking markers S04G03 and C1454 on rice chromosome 9. This finding was the result of our previous analysis of two populations generated by crosses between RIL260 carrying Pi5 and a susceptible cultivar CO39, and between RIL260 and another susceptible cultivar M202 (Jeon et al. (2003) Mol. Genet. Genomics 269: 280-289). To further delineate the Pi5 gene, in the present study, we generated a third mapping population derived from a cross between RIL260 and another susceptible cultivar IR50. Through PCR screening we found that among the susceptible cultivars tested, only IR50 contained the dominant marker JJ817, which was also found in the resistant cultivar RIL260 (data not shown). In contrast, we were not able to amplify a PCR product for JJ817 in other susceptible cultivars including CO39 and M202. We selected IR50 as a mapping parent based on the similarity between the genomic regions for RIL260 and IR50 which we speculated could facilitate recombination in the interval.

To identify rare recombinants within the 170-kb Pi5 locus, a prescreening strategy using the CAPS markers JJ817 and C1454 and a SCAR marker JJ803 was employed in our current analysis of the RIL260/IR50$F_2$ population. Of the 2,014 $F_2$ individuals analyzed, we identified 8 recombinants between JJ817 and JJ803, but none between JJ803 and C1454 (FIG. 1). Using the dominant markers JJ113-T3 and S04G03, we subsequently determined the breakage points of the 8 recombinants we isolated in their progeny ($F_3$) plants, which enabled us to distinguish homozygous from heterozygous genotypes. In total, all 8 lines were found to harbor recombination events between JJ113-T3 and JJ817.

The disease phenotypes resulting from *Magnaporthe oryzae* PO6-6 infection of these 8 identified lines were then determined in the $F_3$ progeny in each case. These experiments further delimited the Pi5 gene to a 130-kb interval between the markers JJ817 and C1454 (FIG. 1). Our previous and current results indicated that both the JJ803 and JJ113-T3 markers cosegregate with Pi5-mediated resistance (FIG. 1). We were unable to further fine-map the R gene at the Pi5 locus.

Example 2

Figure 2:
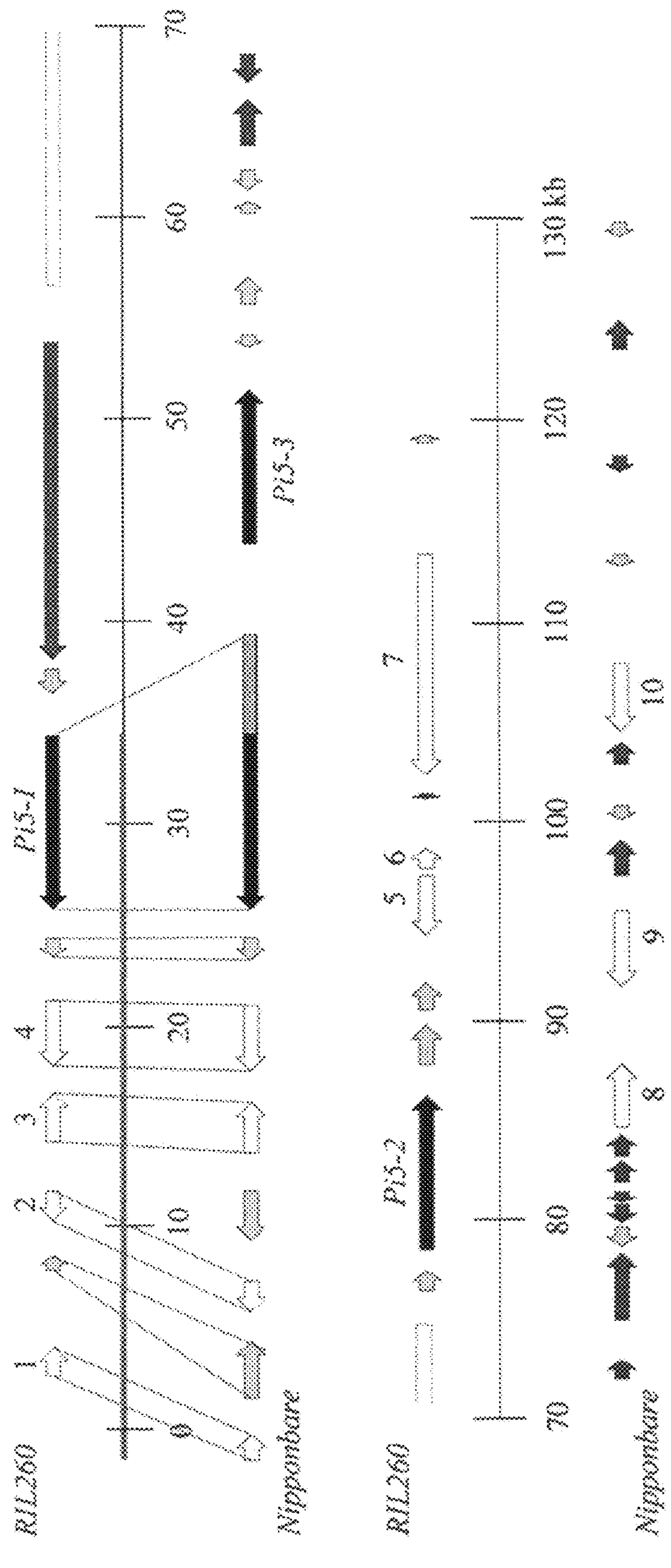
FIG. 2 represents genomic sequence comparison at the Pi5 loci in the RIL260 and Nipponbare cultivars. Predicted ORFs determined by RiceGAAS are shown for both genomes. NB-LRR genes, Pi5-1 alleles, and the Pi5-2 and Pi5-3 genes are indicated by black arrows. The N-terminal region of the Pi5-1Nipponbare allele that is absent in RIL260 is shown in green. Putative transposons and hypothetical genes are indicated by blue and gray arrows, respectively. Open arrows with numbers are predicted to encode the following proteins: 1, putative eukaryotic translation initiation factor; 2, putative GTP-binding protein; 3, putative tetrahydrofolate synthase; 4, putative aldose 1-epimerase; 5, putative histone H5; 6, putative cold-shock DEAD-box protein A; 7 and 10, ankyrin-like proteins; 8 and 9, HGWP-repeat containing proteins. The red dashed line indicates high similarity (>90%) between the RIL260 and Nipponbare ORFs. The chromosomal region that shows little or no homology is indicated by a thin line. The arrows indicate the direction of transcription. A gap in the DNA sequence in RIL260 is indicated by the dotted box.

Genomic Sequence Analysis of the 130-kb Chromosomal Region Containing the Pi5 Locus To identify candidate R genes in the Pi5 locus, 7 BIBAC clones, JJ80, JJ98, JJ106, JJ110, JJ113, JJ120, and JJ123, which covered the 130-kb Pi5 region were selected and sequenced. BLAST searches using these sequences against the public databases and also gene annotation analysis using the RiceGAAS program predicted a total of 18 open reading frames (ORFs) at the Pi5 locus in the RIL260 cultivar: 7 hypothetical proteins, 2 NB-LRR proteins, 2 putative transposon proteins, a putative eukaryotic translation initiation factor, a putative GTP-binding protein, a putative tetrahydrofolate synthase, a putative aldose 1-epimerase, a putative histone H5, a putative cold-shock DEAD-box protein A, and an ankyrin-like protein (FIG. 2). From this genomic sequence analysis, two Pi5 candidate genes that showed homology with NB-LRR resistance genes were identified in RIL260 and designated Pi5-1 and Pi5-2.

The region of approximately 90 kb, from JJ803 to JJ817, of the 130-kb RIL260 Pi5 interval was compared with the corresponding region of the japonica genome represented by the sequenced cultivar Nipponbare (International Rice Genome Sequencing Project 2005; FIG. 2). The resulting sequence analysis showed that the NipponbarePi5 interval contains two NB-LRR genes, Os09g15840 (a Pi5-1 allelic gene) and a gene which was not identified in RIL260, Os09g15850, denoted Pi5-3. In contrast, Nipponbare lacks the corresponding allele of Pi5-2. Notably, the 5 upstream sequences of the Pi5-1 allelic genes of RIL260 and Nipponbare were very different, indicating an extreme sequence divergence within the regulatory sequences of these alleles. In addition, we did not observe significant sequence similarity in any other part of the 90-kb Pi5 intervals in RIL260 and Nipponbare (FIG. 2). These results suggest that the Pi5 resistance locus has significantly diverged between these resistant and susceptible rice cultivars.

We did not compare the Pi5 resistance locus with that of the publicly sequenced indica rice cultivar 93-11 due to a large gap at this locus. In an inoculation experiment, we found that both Nipponbare and 93-11 were susceptible to *Magnaporthe oryzae* PO6-6 (data not shown), indicating neither carries the Pi5 resistance gene.

Example 3

Characterization of Transgenic Rice Plants Expressing Pi5 Candidate Genes

Figure 3:
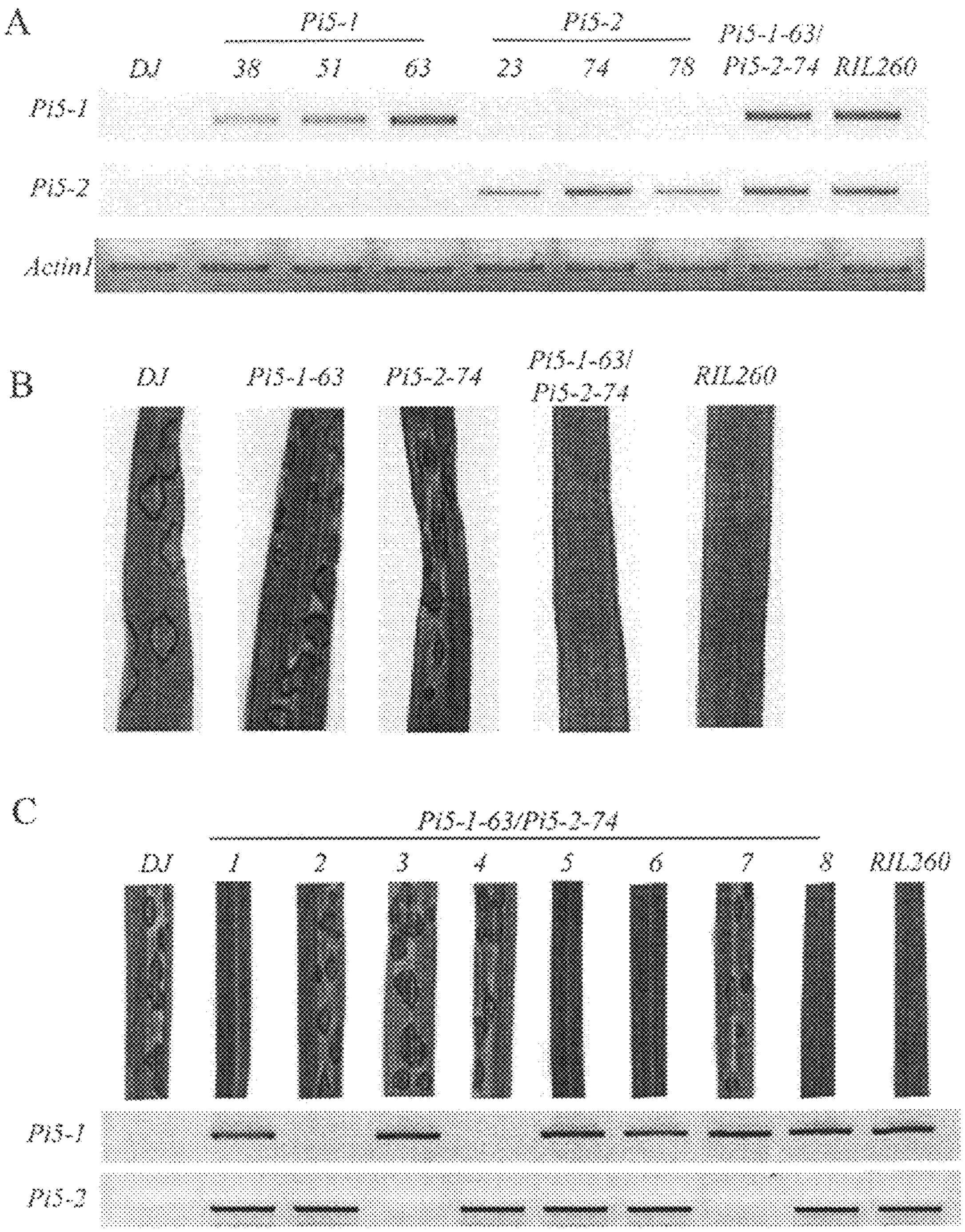
FIG. 3 represents analysis of transgenic rice plants. (A) RT-PCR analysis of Pi5-1, Pi5-2 and Pi5-1/Pi5-2 $F_1$ transgenic rice plants 2 days after inoculation with *Magnaporthe oryzae* PO6-6. The rice Actin1 gene was used as an internal control in these reactions. (B) Disease symptoms in Pi5-1, Pi5-2, and Pi5-1/Pi5-2 $F_1$ transgenic plants 7 days after inoculation with *Magnaporthe oryzae* PO6-6. (C) Genomic DNA PCR analysis and disease reaction of $F_2$ progeny derived from Pi5-1-63/Pi5-2-74 $F_1$ transgenic plants in response to *Magnaporthe oryzae* PO6-6 infection. A resistant cultivar, RIL260 carrying Pi5, and a susceptible cultivar, Dongjin (DJ) lacking the Pi5 gene, were used as controls.

To determine which one of the two candidate genes, Pi5-1 and Pi5-2, is responsible for the Pi5-mediated resistance to *M. oryzae*, we used the genomic clones JJ204 and JJ212 carrying Pi5-1 and Pi5-2, respectively, under the control of their native promoters to transform the susceptible japonica rice cultivar Dongjin using *Agrobacterium*-mediated transformation. RT-PCR analysis of the resulting transgenic lines revealed that 13 of 15 Pi5-1 and 12 of 13 Pi5-2 independently transformed lines expressed their transgenes upon *Magnaporthe oryzae* PO6-6 inoculation (FIG. 3A). The primary transgenic lines ($T_o$) carrying either Pi5-1 or Pi5-2 were inoculated with *Magnaporthe oryzae* PO6-6. Surprisingly, however, none of the 13 Pi5-1 or the 12 Pi5-2 transgenic plants showed resistance to *Magnaporthe oryzae* isolate PO6-6 (FIG. 3B). To confirm these results, we inoculated $T_1$ progeny from these $T_o$ lines and found that all progeny were susceptible to the *Magnaporthe oryzae* isolate to the same extent as the wild-type control Dongjin cultivar. This indicates that neither Pi5-1 nor Pi5-2 alone confers resistance to *Magnaporthe oryzae* PO6-6.

Example 4

Characterization of Transgenic Rice Plants Expressing Both Pi5-1 and Pi5-2

Because recent reports (Sinapidou et al. (2004) Plant J. 38: 898-909) have demonstrated that the presence of two R genes is required for resistance to pathogen infection, we decided to test plants expressing both candidate genes for blast resistance. We therefore generated transgenic plants carrying both Pi5-1 and Pi5-2 by crossing a highly susceptible homozygous Pi5-I line #63 (Pi5-1-63) with the highly susceptible homozygous Pi5-2 line #74 (Pi5-2-74). Gene expression analysis revealed that the $F_1$ plants resulting from the cross expressed both the Pi5-1 and Pi5-2 genes upon *Magnaporthe oryzae* PO6-6 inoculation (FIG. 3A). Strikingly, the 23 of Pi5-1-63/Pi5-2-74 $F_1$ plants tested all displayed complete resistance to *Magnaporthe oryzae* PO6-6. Transgenic lines carrying either Pi5-1 or Pi5-2 were susceptible as previously determined (FIG. 3B).

To confirm this finding, we inoculated the $F_2$ progeny plants from the Pi5-1-63/Pi5-2-74 $F_1$ lines with the *Magnaporthe oryzae* isolate PO6-6. Of the 72 $F_2$ progeny tested, 37 of these carried both transgenes and conferred resistance to *Magnaporthe oryzae* PO6-6. In contrast $F_2$ progeny lacking both Pi5-1 and Pi5-2 were susceptible (FIG. 3C). RT-PCR analysis demonstrated that the Pi5-1-63/Pi5-2-74 lines expressed their transgenes at levels that were similar to RIL260 before and after *Magnaporthe oryzae* PO6-6 inoculation. To test if Pi5-1 and Pi5-2 are required for resistance to other *Magnaporthe oryzae* isolates, we inoculated the transgenic plants with four additional isolates incompatible with Pi5. These isolates displayed distinct virulence patterns on rice lines carrying different single R genes, validating that these are indeed different *Magnaporthe oryzae* isolates. We found that transgenic plants coexpressing Pi5-1 and Pi5-2 were resistant to all of the tested *Magnaporthe oryzae* isolates. The resistance donor RIL260 and the monogenic line IRBL5-M carrying Pi5 were also resistant to these 4 isolates. In contrast, Dongjin and plants carrying either Pi5-1 or Pi5-2 only were susceptible to the tested *Magnaporthe oryzae* isolates (Table 2). These results demonstrate that the two NB-LRR genes Pi5-1 and Pi5-2 are required for Pi5-mediated resistance to *Magnaporthe oryzae* isolates.

TABLE 2

Disease reactions of Pi5 transgenic plants to *Magnaporthe oryzae* isolates

| Isolate | Dongjin | RIL260 | IRBL5-M | Pi5-1-63[a] | Pi5-2-74[a] | Pi5-1-63/Pi5-2-74[a] |
|---|---|---|---|---|---|---|
| PO6-6 | S[b] | R[b] | R | S | S | R |
| KJ105a | S | R | R | S | S | R |
| KJ107 | S | R | R | S | S | R |
| KJ401 | S | R | R | S | S | R |
| R01-1 | S | R | R | S | S | R |
| KI215 | S | R | S | S | S | S |

[a]Transgenic lines.
[b]R, resistant; S, susceptible.

The Pi5 monogenic line IRBL5-M is susceptible to *Magnaporthe oryzae* KI215. Genomic sequence analysis indicated that IRBL5-M genomic region carrying Pi5 is identical to that of RIL260 (data not shown). In addition, RT-PCR analysis further demonstrated that IRBL5-M expresses both Pi5-1 and Pi5-2 at levels similar to RIL260 either before or after *Magnaporthe oryzae* PO6-6 inoculation. Based on these results, we hypothesized that transgenic plants expressing both Pi5-1 and Pi5-2 would also be susceptible to *Magnaporthe oryzae* KI215. Indeed, our inoculation result showed that transgenic plants expressing both Pi5-1 and Pi5-2 are susceptible to *Magnaporthe* oryzae KI215. In contrast, RIL260 was found to be resistant to *Magnaporthe oryzae* KI215, indicating that it may contain an additional R gene that confers resistance to this isolate (Table 2).

Example 5

Characterization and Phylogenetic Analysis of the Proteins Encoded by Pi5-1 and Pi5-2

Figure 4:
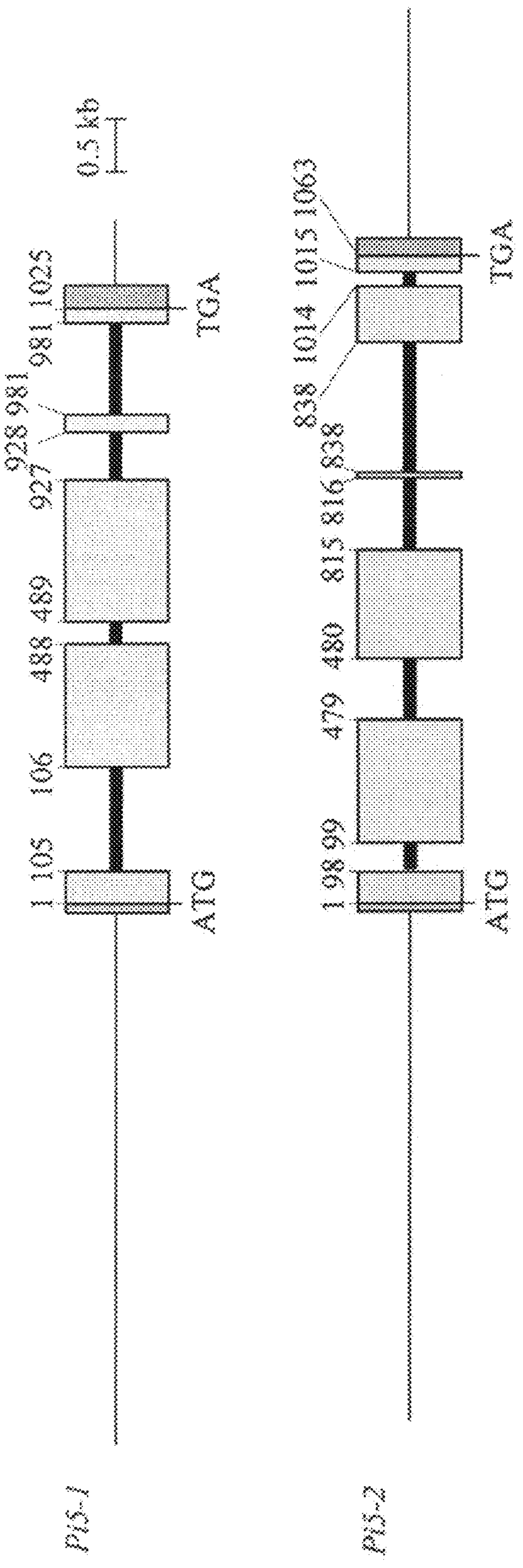
FIG. 4 represents genomic structure of the Pi5-1 and Pi5-2 genes and their gene products. Exons are indicated by light gray boxes and introns are indicated by bold lines. 5'- and 3'-untranslated regions (UTR) are indicated by dark gray boxes. ATG and TGA denote the translation initiation and stop codons, respectively and the numbers indicate the amino acid positions.

To isolate the cDNA clones corresponding to both Pi5 genes under study, a cDNA library for RIL260 was constructed with the Uni-ZAP XR vector using mRNA isolated from rice leaves collected at 24 and 48 hr after inoculation with *Magnaporthe oryzae* PO6-6. This library was screened using a colony hybridization methodology using gene-specific regions of Pi5-1 and Pi5-2 as probes. We identified 7 and 5 cDNA clones for Pi5-1 and Pi5-2, respectively. Sequence analysis further revealed that 3 of the Pi5-1 cDNA clones contained an entire open reading frame (ORF), whereas the others lacked an N-terminus encompassing an ATG translation initiation codon. Among the three full ORF clones, the longest clone (#1-7) was fully sequenced. These experiments revealed that Pi5-1 encodes a protein of 1,025 amino acids and that the ORF is flanked by 5'- and 3'-untranslated regions of 70 and 220 bp, respectively (GenBank accession no. EU869185; FIGS. 4 and 5). Sequence analysis of the Pi5-2 clones revealed that 3 of the 5 clones contained an entire ORF. Among these, the longest clone (#2-4) was further characterized by sequencing. This analysis indicated that Pi5-2 encodes an ORF of 1,063 amino acids and that this ORF is flanked by 5'- and 3'-untranslated regions of 73 and 164 bp, respectively (GenBank accession no. EU869186; FIGS. 4 and 6).

Comparison of their deduced amino acid sequences revealed that both Pi5-1 and Pi5-2 encode an N-terminal CC, a centrally located NB and LRR, and also C-terminal regions (FIGS. 5 and 6). A conserved domain search using the Pfam and SMART databases predicted that residues 109-576 of Pi5-1 and 109-567 of Pi5-2 contain an NB domain, which is a signaling motif shared by plant R gene products. The conserved internal domains characteristic of NB-containing R gene products were also identified in Pi5-1 and Pi5-2, including the P-loop, kinase-2, RNBS-B, GLPL, RNBS-D, and MHDV domains. Additional analysis using the Paircoil2 program (http://groups.csail.mit.edu/cb/paircoil2/) predicted a potential CC domain with a threshold 0.1 between amino acids 31-67 in Pi5-1 and 26-87 in Pi5-2, indicating that these proteins belong to the CC subset of the NB-LRR resistance proteins.

The LRR regions of Pi5-1 and Pi5-2 consist of 24.3 and 22.6% leucine residues, respectively, and contain a series of imperfect repeats (10-12) of various lengths (FIGS. 5 and 6). Of note, a few repeats of the Pi5-1 and Pi5-2 proteins matched the consensus sequence LxxLxxLxxLxLxxC/N/Sx(x) LxxLPxx observed in other cytoplasmic R proteins. The first and third repeat regions of Pi5-1 and the first, third and sixth repeat regions of Pi5-2 contained the xLDL motif that is conserved in the third LRR of many NB-LRR proteins (FIGS. 5 and 6). Notably also, the Pi5-1 and Pi5-2 proteins harbor a unique C terminus that is distinct from those of other NB-LRR proteins, and that does not match any known protein motif.

Sequence comparisons between the cDNA and genomic sequences for these R genes revealed that Pi5-1 and Pi5-2 carry 5 and 6 exons, respectively (FIG. 4). The Pi5 genes have a larger number of introns within their coding regions compared with other cloned rice R genes that confer resistance to *M. oryzae*. Furthermore, the Pi5-1 and Pi5-2 genes contain an intron in both their RNBS-D and MHDV domains.

Example 6

Expression Analysis of the Pi5-1 and Pi5-2 Genes

Figure 7:
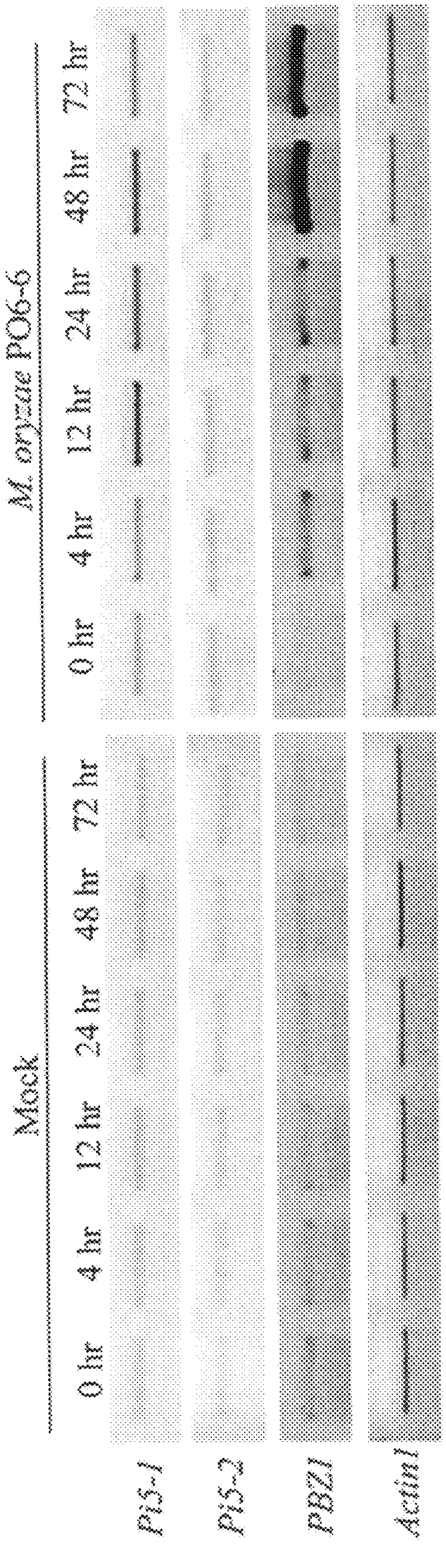
FIG. 7 represents RT-PCR analysis of the Pi5 genes and the PBZ1 gene in the RIL260 cultivar inoculated with *Magnaporthe oryzae* PO6-6. cDNAs prepared from the leaf tissue of RIL260 at 0, 4, 12, 24, 48 and 72 hr after pathogen inoculation were used in the experiment. The rice Actin1 gene was used as an internal control.

To examine whether the expression of the two identified R genes was altered upon pathogen treatment, we performed RT-PCR analysis of these two genes in RIL260, IRBL5-M, and Pi5-1-63/Pi5-2-74 transgenic plants infected with *Magnaporthe oryzae* PO6-6 (FIG. 7). Total RNAs isolated from the leaves of 3 week-old plants harvested at different time points after *Magnaporthe oryzae* PO6-6 inoculation were used for this purpose. The results revealed that Pi5-1 expression increased 12 hr after pathogen challenge, whereas the Pi5-2 gene is constitutively expressed at a low level in RIL260 both before and after infection (FIG. 7). The IRBL5-M and Pi5-1-63/Pi5-2-74 lines also exhibited similar expression patterns of the Pi5 genes. These findings indicated that Pi5-1 and Pi5-2 are both expressed during pathogen infection, suggesting that the encoded proteins are also coexpressed. Transcripts of PBZ1, a pathogen-inducible gene, accumulated to high levels in *M. oryzae*-treated leaves (FIG. 7).

The invention claimed is:

1. A gene that encodes Pi5-1 protein or Pi5-2 protein, wherein the Pi5-1 protein consists of SEQ ID NO: 1 and the Pi5-2 protein consists of SEQ ID NO: 2, for enhancing resistance to Magnaporthe oryzae.

2. The gene according to claim 1, wherein genomic DNA of Pi5-1 consists of the nucleotide sequence of SEQ ID NO: 3 and genomic DNA of Pi5-2 consists of the nucleotide sequence of SEQ ID NO: 4 , and cDNA of Pi5-1 consists of the nucleotide sequence of SEQ ID NO: 5 and cDNA of Pi5-2 consists of the nucleotide sequence of SEQ ID NO: 6.

3. A recombinant vector comprising the gene of claim 1.

4. A plant transformed with the recombinant vector of claim 3.

5. The plant according to claim 4, characterized in that it is a monocot plant.

6. A seed of the plant described in claim 4.

7. A method of increasing resistance to a plant pathogen, comprising the steps of: transforming a plant with the recombinant vector described in claim 3 and then expressing the Pi5-1 gene or Pi5-2 gene in the plant.

8. The method according to claim 7, characterized in that the plant pathogen is Magnaporthe oryzae.

9. The method according to claim 7, characterized in that the plant is a monocot plant.

10. A composition comprising the gene of claim 1 for enhancing resistance to a plant pathogen.

* * * * *

UNITED STATES PATENT AND TRADEMARK OFFICE

CERTIFICATE OF CORRECTION

PATENT NO. : 8,389,803 B2
APPLICATION NO. : 12/733058
DATED : March 5, 2013
INVENTOR(S) : Jong Seong Jeon et al.

It is certified that error appears in the above-identified patent and that said Letters Patent is hereby corrected as shown below:

On the Title Page

Under Item (75) Inventors, the sixth inventor's name is listed as "Hye Kyung" and should read as -- Hye Kyung Kim --.

Signed and Sealed this
Fourth Day of June, 2013

Teresa Stanek Rea
*Acting Director of the United States Patent and Trademark Office*

SEQUENCE LISTING

<160> NUMBER OF SEQ ID NOS: 24

<210> SEQ ID NO 1
<211> LENGTH: 1025
<212> TYPE: PRT
<213> ORGANISM: Oryza sativa

<400> SEQUENCE: 1

```
Met Val Gly Ala Glu Met Leu Val Ala Ala Ala Val Ser Gln Val Ala
1               5                   10                  15

Arg Lys Ile Asn Asp Ile Val Gly Val Ala Gln Gly Glu Val Lys Leu
            20                  25                  30

Cys Cys Asn Phe Ser Asp Asp Leu Glu Gly Ile Lys Asp Thr Leu Val
        35                  40                  45

Tyr Leu Glu Thr Leu Leu Lys Asn Ala Glu Asn Asn Ser Phe Gly Ser
    50                  55                  60

Asp Arg Ala Asn Leu Arg His Trp Leu Gly Gln Ile Lys Ser Leu Ala
65                  70                  75                  80

Tyr Asp Ile Glu Asp Ile Val Asp Gly Tyr Tyr Ser Ser Lys Glu Gln
                85                  90                  95

Phe Asp Gly Gly Ser Tyr Ala Gln Lys Gly Ser Leu Phe Cys Ser Leu
            100                 105                 110

Ser Asn Pro Met Leu Leu Lys Gly Ser Met Val Tyr Lys Met Lys Ser
        115                 120                 125

Lys Arg Glu Met Leu Gln Gln Ser Gln Gln Leu Pro Asn Gln Tyr His
    130                 135                 140

Phe Leu Ser Tyr Ile Asn Ser Ala Val His Tyr Phe Glu Glu Lys Gln
145                 150                 155                 160

Thr Thr Ser Tyr Arg Asn Thr Asp Ile Ala Ile Val Gly Arg Asp Ala
                165                 170                 175

Asp Leu Asp His Leu Met Asp Leu Leu Met Gln Asn Ser Ala Glu Glu
            180                 185                 190

Leu Cys Ile Ile Pro Ile Val Gly Pro Val Gly Phe Gly Lys Thr Ser
        195                 200                 205

Leu Ala Gln Leu Val Phe Asn Asp Thr Arg Thr Glu Val Phe Ser Phe
    210                 215                 220

Arg Ile Trp Val His Val Ser Met Gly Asn Ile Asn Leu Glu Lys Ile
225                 230                 235                 240

Gly Arg Asp Ile Val Ser Gln Thr Thr Glu Lys Ile Glu Gly Asn Met
                245                 250                 255

Gln Leu Gln Ser Ile Lys Asn Ala Val Gln Arg Val Leu Asn Lys Tyr
            260                 265                 270

Ser Cys Leu Ile Ile Ile Asp Ser Leu Trp Gly Lys Asp Glu Glu Val
        275                 280                 285

Asn Glu Leu Lys Gln Met Leu Leu Thr Gly Arg His Thr Glu Ser Lys
    290                 295                 300

Ile Ile Val Thr Thr His Ser Asn Lys Val Ala Lys Leu Ile Ser Thr
305                 310                 315                 320

Val Pro Leu Tyr Lys Leu Ala Ala Leu Ser Glu Asp Asp Cys Leu Lys
                325                 330                 335

Ile Phe Ser Gln Arg Ala Met Thr Gly Pro Gly Asp Pro Leu Phe Arg
            340                 345                 350

Glu Tyr Gly Glu Glu Ile Val Arg Arg Cys Glu Gly Thr Pro Leu Val
        355                 360                 365
```

-continued

```
Ala Asn Phe Leu Gly Ser Val Val Asn Ala Gln Arg Gln Arg Arg Glu
    370                 375                 380

Ile Trp Gln Ala Ala Lys Asp Glu Glu Met Trp Lys Ile Glu Glu Asp
385                 390                 395                 400

Tyr Pro Gln Asp Lys Ile Ser Pro Leu Phe Pro Ser Phe Lys Ile Ile
                405                 410                 415

Tyr Tyr Asn Met Pro His Glu Leu Arg Leu Cys Phe Val Tyr Cys Ser
            420                 425                 430

Ile Phe Pro Lys Gly Thr Val Ile Glu Lys Lys Lys Leu Ile Gln Gln
        435                 440                 445

Trp Ile Ala Leu Asp Met Ile Glu Ser Lys His Gly Thr Leu Pro Leu
    450                 455                 460

Asp Val Thr Ala Glu Lys Tyr Ile Asp Glu Leu Lys Ala Ile Tyr Phe
465                 470                 475                 480

Leu Gln Val Leu Glu Arg Ser Gln Asn Asp Ala Glu Arg Ser Ser Ala
                485                 490                 495

Ser Glu Glu Met Leu Arg Met His Asn Leu Ala His Asp Leu Ala Arg
            500                 505                 510

Ser Val Ala Gly Glu Asp Ile Leu Val Ile Leu Asp Ala Glu Asn Glu
        515                 520                 525

Arg Asn Ala Arg Tyr Cys Asn Tyr Arg Tyr Ala Gln Val Ser Ala Ser
    530                 535                 540

Ser Leu Glu Ser Ile Asp Arg Lys Ala Trp Pro Ser Lys Ala Arg Ser
545                 550                 555                 560

Leu Ile Phe Lys Asn Ser Gly Val Asp Phe Glu His Val Ser Glu Val
                565                 570                 575

Leu Ser Val Asn Lys Tyr Leu Arg Val Leu Asp Leu Ser Gly Cys Cys
            580                 585                 590

Val Gln Asp Ile Pro Ser Pro Ile Phe Gln Leu Lys Gln Leu Arg Tyr
        595                 600                 605

Leu Asp Val Ser Ser Leu Ser Ile Thr Ala Leu Pro Leu Gln Ile Ser
    610                 615                 620

Ser Phe His Lys Leu Gln Met Leu Asp Leu Ser Glu Thr Glu Leu Thr
625                 630                 635                 640

Glu Leu Pro Pro Phe Ile Ser Asn Leu Lys Gly Leu Asn Tyr Leu Asn
                645                 650                 655

Leu Gln Gly Cys Gln Lys Leu Gln Arg Leu Asn Ser Leu His Leu Leu
            660                 665                 670

His Asp Leu His Tyr Leu Asn Leu Ser Cys Cys Pro Glu Val Thr Ser
        675                 680                 685

Phe Pro Glu Ser Ile Glu Asn Leu Thr Lys Leu Arg Phe Leu Asn Leu
    690                 695                 700

Ser Gly Cys Ser Lys Leu Ser Thr Leu Pro Ile Arg Phe Leu Glu Ser
705                 710                 715                 720

Phe Ala Ser Leu Cys Ser Leu Val Asp Leu Asn Leu Ser Gly Phe Glu
                725                 730                 735

Phe Gln Met Leu Pro Asp Phe Phe Gly Asn Ile Tyr Ser Leu Gln Tyr
            740                 745                 750

Leu Asn Leu Ser Lys Cys Leu Lys Leu Glu Val Leu Pro Gln Ser Phe
        755                 760                 765

Gly Gln Leu Ala Tyr Leu Lys Ser Leu Asn Leu Ser Tyr Cys Ser Asp
    770                 775                 780

Leu Lys Leu Leu Glu Ser Phe Glu Cys Leu Thr Ser Leu Arg Phe Leu
```

```
785                 790                 795                 800

Asn Leu Ser Asn Cys Ser Arg Leu Glu Tyr Leu Pro Ser Cys Phe Asp
                805                 810                 815

Lys Leu Asn Asn Leu Glu Ser Leu Asn Leu Ser Gln Cys Leu Gly Leu
            820                 825                 830

Lys Ala Leu Pro Glu Ser Leu Gln Asn Leu Lys Asn Leu Gln Leu Asp
        835                 840                 845

Val Ser Gly Cys Gln Asp Cys Ile Val Gln Ser Phe Ser Leu Ser Thr
    850                 855                 860

Arg Ser Ser Gln Ser Cys Gln Arg Ser Glu Lys Ala Glu Gln Val Arg
865                 870                 875                 880

Ser Arg Asn Ser Glu Ile Ser Glu Ile Thr Tyr Glu Glu Pro Ala Glu
                885                 890                 895

Ile Glu Leu Leu Lys Asn Asn Pro Ser Lys Asp Leu Ala Ser Ile Ser
            900                 905                 910

His Leu Asn Glu Asp Arg Ile Glu Glu Pro Glu Val Val Thr Glu Pro
        915                 920                 925

Ser Ala Thr Arg Gly Met Val Gln Gln Ile Pro Gly Asn Gln Leu Ser
    930                 935                 940

Ser Pro Ser Ser His Leu Ser Ser Phe Ala Ser Ser Ser Ala Pro Phe
945                 950                 955                 960

Ala Ser Ser Ser Ser Asp Thr Ser Thr Ser Glu His Pro Val Pro Asn
                965                 970                 975

Glu Glu Ala Ala Ala Leu Thr Val Pro Arg Ser Lys Glu Lys Cys Asp
            980                 985                 990

Asn Thr Pro Met Pro Val Lys Asp Gly Leu Ile Ser Glu Asp Asp Ala
        995                 1000                1005

Pro Val His Leu His Gln Lys Pro Leu Gln Ala Thr Ala Met Ala Ala
   1010                1015                1020

Ile
1025


<210> SEQ ID NO 2
<211> LENGTH: 1063
<212> TYPE: PRT
<213> ORGANISM: Oryza sativa

<400> SEQUENCE: 2

Met Ala Thr Ala Gly Ala Ala Val Asp Arg Leu Leu Arg Arg Leu Ala
  1               5                  10                  15

Ser Gly Ala Gly Arg Leu Glu Leu Pro Ser Ser Ile Asp Glu Asp Met
             20                  25                  30

Ala His Val Lys Arg Thr Leu Ala Arg Leu Gln Asp Val Leu Leu Thr
         35                  40                  45

Val Glu Gly Lys Tyr Phe Lys Met Gly Ala Glu Val Gln Glu Trp Met
     50                  55                  60

Arg Lys Ile Lys Gln Ile Ala Tyr Gly Ile Gln Asp Leu Leu Asp Glu
65                  70                  75                  80

Phe Glu Asp Ser Ser Gly Thr Gly Ser Gln Arg Asn Gly Ser Arg Ile
                 85                  90                  95

Ser Glu Gly Thr Leu Ser Cys Ser Ser Ala Pro Phe Phe Cys His Leu
            100                 105                 110

Ser Arg Ser Gln Arg Ile Arg Val Leu Lys Arg Lys Leu Asp Gln Ser
        115                 120                 125

Thr Lys Asp Thr Ser Val Phe Ser Leu Leu Gln His Ser Leu Ser Asn
```

-continued

```
    130                 135                 140

Leu Asp Lys Ser Asn Glu Gln Glu Val Leu Leu His Arg Thr Glu Ile
145                 150                 155                 160

Ile Gly Arg Asp Thr Asp Lys Glu Asn Ile Lys Asn Leu Leu Leu Gln
                165                 170                 175

Asn Asp Val Asp Lys Leu Pro Ile Ile Pro Ile Val Gly Leu Ala Gly
            180                 185                 190

Leu Gly Lys Thr Ala Val Ala Lys Leu Ile Phe His Glu Gln Gly Glu
        195                 200                 205

Gly Trp Asn Phe Asp Gln Arg Ile Trp Val His Leu Asp Lys Lys Leu
    210                 215                 220

Asp Leu Asn Lys Ile Ala Asn Ser Ile Ile Ser Gln Val Asn Gln Ser
225                 230                 235                 240

Val Asp Thr Thr Lys Asn Gln Ile Gln Asn Asn Leu Gln Phe Lys Arg
                245                 250                 255

Asn Cys Leu Gln Glu Val Leu Cys Asp Gln Ser Ser Leu Ile Val Leu
            260                 265                 270

Asp Asp Leu Phe Ser Thr Glu Glu Asn Gln Ile Ala Glu Leu Lys Glu
        275                 280                 285

Met Leu Arg Gly Thr Lys Lys Gly Thr Lys Ile Ile Val Thr Thr Ser
    290                 295                 300

Ser Glu Ile Ser Ala Glu Leu Ile His Thr Val Pro Pro Tyr Lys Leu
305                 310                 315                 320

Gly Pro Leu Ser Glu Gly Asp Cys Ser Thr Ile Phe Cys Gln Arg Ala
                325                 330                 335

Phe Gly Asp Gly His Glu Asn Ser Ser Leu Thr Glu Ile Ala Lys Gln
            340                 345                 350

Ile Val Lys Arg Cys Glu Gly Ile Pro Ala Val Ala Tyr Ser Leu Gly
        355                 360                 365

Ser Leu Val Arg Asn Lys Asn Lys Glu Ala Trp Leu Tyr Ala Arg Asp
    370                 375                 380

Lys Glu Ile Trp Glu Leu Pro Thr Leu Phe Pro Asn Gly Phe Glu Leu
385                 390                 395                 400

Leu Ala Ser Phe Ser Glu Met Tyr Ile Cys Met Pro Ser Ala Leu Lys
                405                 410                 415

Ser Cys Phe Ala Tyr Leu Ser Thr Ile Pro Lys Gly Thr Ile Ile Asp
            420                 425                 430

Arg Glu Lys Leu Ile Glu Gln Trp Ile Ala Leu Asp Met Val Gly Ser
        435                 440                 445

Lys His Gly Thr Leu Pro Ala Tyr Val Gln Gly Glu Met Phe Ile Gln
    450                 455                 460

Gln Leu Leu Ser Ile Ser Phe Leu Gln Val Arg Asn Lys Pro Ser Ala
465                 470                 475                 480

Thr Arg Ile Arg Asp Thr Asn Gln Ser Lys Glu Leu Arg Ile His Asn
                485                 490                 495

Leu Val His Asp Phe Ala Met Tyr Val Ala Arg Asp Asp Leu Ile Ile
            500                 505                 510

Leu Asp Gly Gly Glu Lys Ala Ser Ser Leu Arg Lys Asn Ile His Val
        515                 520                 525

Phe Tyr Gly Val Val Asn Asn Asp Ile Gly Gln Ser Ala Leu Arg Lys
    530                 535                 540

Gly Leu Leu Ser Ser Ala Arg Ala Val His Phe Lys Asn Cys Lys Ser
545                 550                 555                 560
```

```
Glu Lys Leu Leu Val Glu Ala Phe Ser Val Leu Asn His Leu Arg Val
                565                 570                 575

Leu Asp Leu Ser Gly Cys Cys Ile Val Glu Leu Pro Asp Phe Ile Thr
            580                 585                 590

Asn Leu Arg His Leu Arg Tyr Leu Asp Val Ser Tyr Ser Arg Ile Leu
        595                 600                 605

Ser Leu Ser Thr Gln Leu Thr Ser Leu Ser Asn Leu Glu Val Leu Asp
    610                 615                 620

Leu Ser Glu Thr Ser Leu Glu Leu Leu Pro Ser Ser Ile Gly Ser Phe
625                 630                 635                 640

Glu Lys Leu Lys Tyr Leu Asn Leu Gln Gly Cys Asp Lys Leu Val Asn
                645                 650                 655

Leu Pro Pro Phe Val Cys Asp Leu Lys Arg Leu Glu Asn Leu Asn Leu
            660                 665                 670

Ser Tyr Cys Tyr Gly Ile Thr Met Leu Pro Pro Asn Leu Trp Lys Leu
        675                 680                 685

His Glu Leu Arg Ile Leu Asp Leu Ser Ser Cys Thr Asp Leu Gln Glu
    690                 695                 700

Met Pro Tyr Leu Phe Gly Asn Leu Ala Ser Leu Glu Asn Leu Asn Met
705                 710                 715                 720

Ser Lys Cys Ser Lys Leu Glu Gln Leu Pro Glu Ser Leu Gly Asp Leu
                725                 730                 735

Cys Tyr Leu Arg Ser Phe Asn Leu Ser Gly Cys Ser Gly Leu Lys Met
            740                 745                 750

Leu Pro Glu Ser Leu Lys Asn Leu Thr Asn Leu Glu Tyr Ile Asn Leu
        755                 760                 765

Ser Asn Ile Gly Glu Ser Ile Asp Phe Asn Gln Ile Gln Gln Leu Arg
    770                 775                 780

His Ile Leu Lys Lys Thr Phe Phe Ser Gly Asp Ile Gly Gly Ser Glu
785                 790                 795                 800

Leu Gln Thr Cys Glu His Ala Ala Asp Ser Ala Asp Ser Lys Lys Glu
                805                 810                 815

Ile Thr Met Asp Phe Ser Ala Asn Leu His Gly Asn Ile Thr Leu Pro
            820                 825                 830

Pro Lys Cys Ser Thr Glu Glu Lys Ser Gly Glu Asn Ser Glu Arg Phe
        835                 840                 845

Leu Ser Ala Ala Val Arg Glu Asp Ser Ser Ser Thr Asp Val Ser Thr
    850                 855                 860

Tyr Val Lys Pro Val Val Ser Ser Leu Ile Gly Val Leu Arg Arg Pro
865                 870                 875                 880

Thr Arg Leu Asp Val Pro Ala Gly Ala Met Ala Ser Gln Val Gly Leu
                885                 890                 895

Ala Gln Met Pro Ser Ser Asn Asn Gly Lys Ala Gly Pro His Pro Thr
            900                 905                 910

Met Ala Ala Ala Gln Thr Pro Glu Ile Asp Gln Pro Val His Lys Arg
        915                 920                 925

Val Arg Trp Asp Asp Ile Ile Asp Tyr Ser Arg Pro Pro Asn Ser Lys
    930                 935                 940

Pro Ala Arg Ser Ala Ser Leu Val Gln Ser Thr Asp Leu Ser Thr Pro
945                 950                 955                 960

Lys Lys Ser Tyr Lys Lys Ile His Ser Met Pro Val Val Tyr Ser Ser
                965                 970                 975

Ile Pro Lys Gly Ser Ser Gly Gly Thr Tyr Leu Met Pro Ala Lys Ala
            980                 985                 990
```

```
Ile Ala Ser Ser Tyr Arg Arg Tyr Ser Pro Gln Arg Trp Glu Gln His
        995                 1000                1005

Ile Gly Tyr Gln Gly Thr Asp Glu Asp Glu Leu Met Val Val Pro Pro
   1010                1015                1020

Phe Gly Glu Trp Asp Gln Ser Pro Thr Leu Arg Lys Ser Asp Phe Arg
1025                1030                1035                1040

Tyr Glu Lys Val Phe Ala Lys Leu Thr Glu Glu Lys Met Ser Gly Gln
               1045                1050                1055

Arg Gln Lys Pro Gln Gln Val
1060
```

<210> SEQ ID NO 3
<211> LENGTH: 11516
<212> TYPE: DNA
<213> ORGANISM: Oryza sativa

<400> SEQUENCE: 3

```
aagcttgaaa gtgtgtgaag aaatgaagaa agtgaagtct acttatagga caggtataac     60

ggttatgaga agtggaaatg tccgaactgc cccgcaaccg ccatcaggga gtgatctgga    120

gcgtccacgc caaaccccag gatcaacggt gatcaccagg gttcggctga acctgggctg    180

ggccagatgg cttccaaacc tagtctgggt ctcctcctcg acctgcctta tccaattctt    240

gcaattttgg gatgtttctt tagtagttta aaagcccatt cttgcattga tagatttctc    300

cttcactttt agtctggatt tcctcccaac ttctgggttt atcacctgca taaaaatata    360

catcaacaat tgtggaatat gtgagtttta acacctatca ctatgttgga tattttatta    420

tctggacttt atgcagacgt tgacggtata gatttggcat ttaacagtcg ccaacattat    480

acaatcgggt aaatagtatt gatgtattcc atgaatctgt gtatagaagg tatgccatat    540

ccttgacact gacaccatat gtgtttccgt ttttgagaaa acatttccat ttccaaaaat    600

ttctgaccaa cactctctat ttccgaaaac tcatctgaaa tccgaaaact tttcaaaccg    660

ttttcatccc agtaatgaat ggcaggctct acgtgcagac ccacaaatgc tccacaaaga    720

tctcaaaaaa tttatcgtat aaatttcata cgtagactaa atttcacaaa aattcacttg    780

tgtacccatt gaggtatgta ttttgttttc aaaaaaaaac acagtttacc ttgtggtgct    840

cgggacatcg gccggagctc atgatcataa tggagtcagt cagggtggct actggagctt    900

atggcggagg aggtcagggt ggtgggacgt ggggcagagt ttagtccggt cggcaaccag    960

agctccgaga ggagatctgg gcagtagtga gagaagggtc aggaggcgcc agagtggcca   1020

cgacggaggc tgggaaagcg atgccgaaca gcaaagcatg cgttgaagta ggcggggtgg   1080

cagcagcctc ggggcggagc gggcatggaa caagggtaga gctggagtcg gtggccggct   1140

actgagacca ttcacagtgc gtcaccaagt tttgatattc ttcacatgcc acgtagatca   1200

gagcggtatt agccacatgt tacatagtgc aaaactctac aagaccacat atgggttgct   1260

tgtagtgggt cccactaata ccacttttac acttctcttt ttacttttcc cctctcctct   1320

ctcccctctc ttcctttccc caccggccac cgcagagagc cgggcggaga cggaggttgc   1380

gggggtcggg cggagcggcg gctcaagcgg aggtcgtgga ggcgagcagg agacggcgcc   1440

gggccgagtg gcgacggcgg tggggcctag caccgtgcct cccctcctcc tcctcctcta   1500

gtggtggcga atcgaggaag ccgccgccgc cgcgccccac ctcttcatct gatgcgggcg   1560

ggaagctgcc gccaccgccg tcgggcagat ccagatctcc ggcctccgtg tcgggcggct   1620

acgcggcggc gggcgtcggc gtcggtcagc gccctcctca cctggccagc ccaccgacta   1680
```

-continued

```
gccctaccgt cgtcatcatc cctggtcagc accctcctcc cctggcattc ggctgcctca   1740
cccctctcct ctctctcctc tagcggtggt gtgggtccca cctgtgggtc cctctgagac   1800
gaagaacgcg tagtcaactt tggctacgcg cggagctgag gaacgcacac gattggataa   1860
agtggcaaag gaatatttgc ttttttggtt gaggctaaat gctacgtaga tctactgtga   1920
atggcctgat ggcgcagcgg ctctcttgcg ggacagagtg ggacgtgcac gacgagaaat   1980
ttcctcttgc atgaataacc cacggatgta ggcctcctta actaggagct acgaggtggg   2040
atttgggagg ctttttctat ttcaaggctt aaagcctatc caatatgatc tctaatctta   2100
aaatttagtg tttatttttg aaaaaaagtt ggctccaata attttcctaa ttagcttcca   2160
aaaattggaa tcttactccc tatccttctc gctctccact agtggagaag cgtgctagtt   2220
cttaacacac gcatgggtgg agggatcaca tggatattat ggaaatatcc tcatggactg   2280
gtgattaaca tagtcctact aggagagaat tgagtttatt ctatatcgtt atcgacgttt   2340
ggtatcacga ctacgttatt tggatggtat ggggatcatc ggtactagag tatatgcgag   2400
attgaggtaa aagagatgga gacagatatt tttatactgg ttcgcccctt atctaacagg   2460
taatagccct acatcctgtt ggctaaagcc ggtattgctc ttattcatct gaatcgcaca   2520
agtataatat ttaggataac ctgtctagct gtcatcgact tggcggcatg gataaccaac   2580
tcgtagtcga tgacggggta gtatttctct tcgaatatga actcgtcgag atcagagatg   2640
gctctagatc tctcttgccg gtctcaggag gcaccagatg gggtatgcct aggctaatct   2700
ctaatgtcga tatttagcgg cgtattggct tgtgtgtatg ttatgtgttg tggctcgtca   2760
tctctcctcc tagggggctt gtatttatac ccatagatgc ccccttgtct aagtagaact   2820
agggagataa atatggatac gatccgagta gtccttgtcg tttccatata gaactctttt   2880
tgtcctttct tatccgaaac tccttttata tacgaggtat gattccatat aagacatggt   2940
atatggtggg ccctgccgag cttagtcagg aatgtggtat ccacaaccct gacaatcatg   3000
cagggttcat tgtctccgag ttctacgcgg agactaagac aactcaaggt ataaaaggcg   3060
cactctctaa ggggttcaaa agagcaaatc atagcacgaa cacacccacc atagtttacg   3120
aagccagagg ctgtgaagcc tactcgccag gagatcttgt cgactcatct cgacaaggat   3180
ctcgccggta acgctggatt catctcttct ctttgtactc cgtggtttcc atatcaatct   3240
catataaact ggattatggt tattatctta cgaggggtct aaaccagtat aatctttgtc   3300
tctctgattg ttttaatatc gtatcatgta gatcctcata ccaacttacc ctaatacact   3360
atttatccga tctacaggta tcccctatcg acaataggta tataagatat tataaaaaag   3420
atggagacat atgtgagctg atgatttagg ctgcattcgt tgcagcttct ttccaaccca   3480
tctccctcgt tttccgtgcg catgcttttc aaactgctaa acggtgcgtt ttttacaaaa   3540
agtttatata cgaaagttgc ttaaaaaaat catattgatc catttttttaa aaagatagca   3600
aaaaattaag taatcacacg ctaatggact actctgtttt ccgtgccgga ggatagcttt   3660
cccaacccag ggaaacgaac ccaaccttag gtgtgttcat tgctaggtgt tcccaacccc   3720
tctcccttat attccgtgcg catgcttttc aaactgttaa acggtgtgtc tctttttaaa   3780
aaatttctat acgaaagttg ctaaaaaaat catatcaata catttttgaa aaaaaaagct   3840
aatacttaat taatcacgta cgtactaata gaccgcttcg ttttctatgc gcagaagatt   3900
tgttcccaac ccccacaaca aacacagcct taacatgctt gcatttaaaa agctataaaa   3960
tttaataaat tataaaatta tagataatat aacatgctta cttgatgtga cactttacct   4020
gttaagtttt aggagtcggt gtttagattc aaactttttt tttcaaactt ccaacttttc   4080
```

-continued

```
catcagatca aatgtttggg cacatgcatt cagcaataaa tgtggacaaa aaaaaaccag   4140
ttgtacagtt tgcatgtaaa tcacgagatg aatcttttga gcctaattac gtcatgattt   4200
gacaatgtgg tgctaaagta aatatttact aatgacagat taattaggtt taatagattt   4260
gtctcgcagt ttacaggcga aatatataat tttttttgtt attagtttat atttaatact   4320
taaaatgtat gtccatatac ttaaaaaaat tttgtaccac gaactaaaca cagccaagtg   4380
gactctaact ctctctctct ctatatatat atatatatat atatagtaat gtgttcgtat   4440
gtcctggata gaaactcatt tcctccgcat agaaaacgga gcggtctatt aatacgtgat   4500
taattaagta ttagctattt ttttcgaaaa taaattaatt taattttttta aataacattt   4560
atatagaaac tttttaaaaa acacgttgat taaccatttg aaaagcgtgc gtgcacgcgg   4620
cgtgaaaaat gaggcagaga tgttgtgaaa aggagtgccg aacacagtca aagcctcagg   4680
tggtgtttgg atccagggac ttaacttaaa ctttagtccc tatatttaga cactaattta   4740
tagtattaaa tatagactac ttataaaact aattacataa atgaaagcta attcacgaga   4800
caattttttt aagcctaatt aatccataat taaagaatgt ttactgtagc atcacatagg   4860
ctaatcatgg attaattaga cttaatagat tcatctcgtg aattagtcca agattataga   4920
tgggctttat taatagtcta cgtttaatat ttataattaa ttttcaatcc aatatgatag   4980
gacttaaaat ttagtcccat ctacagggtc agaggattcg gtcggtctca gggcagtcct   5040
ctccgtataa cgcagcgccc gatatttttt atgggcataa atagtctgat tgctactgta   5100
gcattttgtt caactaactc cccaatgggc aatggctagt cgtcgagtgt cagtagtcaa   5160
gagtagactc cgcttcgctt cgccgtacct tctctcttct cgttctccta tttcacaaat   5220
cacaaccgga ttgctttctt ccttcctccg gtctggtccc caacctccgc ggcagccatg   5280
gttggcgccg agatgcttgt ggccgcggcg gtgagccagg tcgcccggaa gatcaacgac   5340
atcgtggggg tcgcgcaggg cgaggtgaag ctgtgctgca atttcagcga cgatttggag   5400
ggcatcaagg ataccccttgt gtacctggaa accttgctga aaaatgcgga gaataactcc   5460
ttcggaagcg acagggccaa cctgcgccac tggcttggcc agatcaagtc cctggcttac   5520
gatatcgaag atatcgttga tgggtactac tcttccaagg agcagttcga tgggggcagc   5580
tatgcacaga aggtaacaga atctcattcc tttttcttca tcggtaaaat ttcttcaatt   5640
tcaactcaat tttagaatgc cccgcaaaaa aaaaatcaat tttagaatgg atctacatta   5700
atgagatgta gaggtgtatt actatgggca ggggaagcac cgtgtgtgca tccttagtta   5760
ctgcataggc aataagttat cctttccatt gtccaaaaaa attttgaagc aaggaggaaa   5820
agcttgaagc ttagtctttt agttttttct ttttgattat tttgttattt atctcagtta   5880
tgagattagg agtgtatatg cactcgtgta gcttttgtct gtgtgtggat atagaggctg   5940
gatttctatc cattatctta aataaattgt ccaagaaatt tatcagggga aatgcagtta   6000
gatgcaccat tagaattgct tcattgcctg tggaagagtg gaacagctct gagaattgtg   6060
attatgtttt atatatttaa acaatattga ttactagtac tagatttact ctcttttttt   6120
ttccttatga aattccttga tactggtagt agtgagagat aaacctaata attacatgcc   6180
acatacctgt agattgtact atacttcaac acccttttgc aaatagtgag agataaacct   6240
aatacttact tacatgccac atcgtcagag cactcaattc ttttttgttt tggtaagcaa   6300
tcagcttttg cctttacata gacaaaaatt gatcgacgaa tattttgaaa aaaaaaacct   6360
ttgtatttat atggaaaaga aaatgcaagg tactttacca aacaattgtg catctatgat   6420
ctatctgcta tgtaggggtt gataccggcc ttggttcctt gctgcaccaa ctgttattta   6480
```

-continued

```
cctatctcca tttttgttct tccagcaaca atagtatcaa aatactaaat gtctttcctg   6540
actaaggcta ccttcataaa tttacagggg tcattattct gctcgctatc caatccaatg   6600
cttctgaaag gtagcatggt ttataagatg aaatccaaga gagagatgct acagcaaagc   6660
caacagttgc ccaatcagta tcatttcctt tcatatatca attcagctgt gcattatttt   6720
gaggagaagc aaacaacatc atacagaaat actgacattg caattgtcgg gagggatgct   6780
gatttggatc atctcatgga tcttttaatg caaaacagcg ctgaagagct ttgtattata   6840
cccatagttg ggcctgtagg ttttggaaag acaagccttg cacagttagt tttcaatgat   6900
acaagaacag aggtattcag ctttaggata tgggttcatg tttccatggg taatatcaac   6960
cttgaaaaaa ttgggagaga tatagtttca caaactacag aaaaaattga gggaaatatg   7020
cagctgcagt caatcaagaa tgctgttcag cgtgtgctaa ataaatatag ttgcttgatc   7080
ataatagaca gcctttgggg aaaggatgaa gaagtgaatg aattgaagca gatgttgctt   7140
acaggtagac acacagaaag caagatcata gtgaccactc atagcaataa agtagctaag   7200
ctgatttcca ccgttccact gtacaagttg gcagctttat ctgaggatga ttgtttaaaa   7260
atattctctc aaagggcaat gacaggtccg ggtgacccgt tgttcaggga atatggagaa   7320
gaaatcgtta gaaggtgtga aggcacaccc ttggtagcca attttctcgg ttctgtggtg   7380
aatgctcaac gacaaaggcg tgagatttgg caagctgcaa aggatgaaga aatgtggaag   7440
atagaggaag attatcccca agacaaaatt tcaccactat ttccatcatt caagataata   7500
tattataata tgccccatga gctaagatta tgctttgtat attgttcaat cttccctaaa   7560
ggaactgtta tagaaaagaa gaaacttatt cagcaatgga ttgcacttga catgattgag   7620
tccaaacatg gaaccttgcc acttgatgta actgcggaga aatatattga tgaacttaaa   7680
gcaatctatt tccttcaagt tttagagcgg tctcaggtaa gttcatgggt tgctttttac   7740
cttctgtaca tatcctatgt aactagaatg tggttaaata tctccattaa gcatagtagc   7800
ttataccatt gttttatttc taaattctca ataagtttct gtaagaagat tgaccatgat   7860
agaatggcca atagtgatat ctcaacaaac aagtaacact gttttcctcc acagaatgat   7920
gcagaaagat ccagtgcttc tgaggaaatg cttcgcatgc ataacttggc tcatgatctt   7980
gctagatcgg ttgctggtga agatatcctt gttattttag atgccgagaa tgagcgcaat   8040
gccagatatt gcaattaccg ttatgcacag gtgtctgctt ctagtttaga gtcaatcgat   8100
cgcaaggcat ggccttccaa ggcaaggtca ctaattttca agaatagtgg tgtggacttt   8160
gagcatgtca gtgaagttct ttcagtgaac aaatacctgc gtgttttgga tctcagtgga   8220
tgttgtgttc aagatattcc atctcctatc tttcagctga aacaattgag atacctcgac   8280
gtttcatctt tatctattac agcactccct ctgcaaatta gtagctttca taagttacaa   8340
atgttggatc tttcagaaac tgaactaaca gagttgccac cctttataag caacttaaaa   8400
ggactgaatt atttgaatct ccaaggttgc cagaaacttc aacgattgaa tagccttcat   8460
ttgttgcatg atctacatta cctaaacttg tcatgctgcc ctgaagttac tagttttcct   8520
gaatctattg aaaatctgac caaactccgt ttcttgaatc tttctggatg ctctaagctt   8580
tcaacattac ctatcagatt tttggaatca tttgctagcc tctgttcttt ggtagatctt   8640
aacttaagtg gctttgaatt ccaaatgttg cccgactttt ttggcaacat atattcactt   8700
cagtatttaa atctgtcaaa atgtttgaaa cttgaggtat taccacaatc ttttggccaa   8760
cttgcatatc tgaaaagcct aaatctttca tattgttctg atcttaaact gctggaatcc   8820
tttgaatgcc ttacctctct tcggtttttg aatctctcga actgctctag gcttgaatat   8880
```

-continued

```
ttgccatcat gctttgacaa gcttaataat ttagagtctc tgaatttatc acaatgtctt   8940
ggacttaaag cactacctga atcacttcaa aaccttaaaa atcttcagct tgatgtttct   9000
gggtgtcagg attgtatagt acaatccttt tctctaagta ccagaagttc ccagtcctgc   9060
caacggtcgg agaaagctga gcaggtcaga tcaagaaaca gtgaaatttc agagatcact   9120
tatgaggaac ctgctgagat tgaactttta aagaataatc caagtaaaga tttggcctcc   9180
atctcacacc taaatgagga tagaattgag gagcctgaag ttgtcactga ggtaaactta   9240
cattttatta aagaaataaa aacaatttgc ctagtgtttc ctttgaaatt tccttatgtc   9300
aatacttaat ttatctttga tagatttgag ttactggtga ttgagaaagt tgtatgccaa   9360
tttgaaccag tttctcacta ccaactgaaa atgatgacga acggaaactt tattgtagtt   9420
gtgctcgaat tgaagatccc ttttctaatg aggtgatcta attgggtacc agaacatgaa   9480
tcatactttt ttcagtagtt cttaacattt cgtagagaaa atacatgagt gttccttcaa   9540
ttaaaaaact ccctagaggc cagcaagtta taaatttaaa tgggattctc cttattacct   9600
agatttatgt tttcagaaaa ttttgtaata tcatactaac taattgtcca tgtccttgtt   9660
tcttgatgta gccaagtgca actagaggta tggtacaaca gattccagga aaccagctct   9720
catcgccttc atctcatctt tcttcctttg catcaagctc agcgccattt gcatcctcct   9780
cttcggacac ctcaacaagt gagcatccag tgcctaatga agaggcggca ggtatggtac   9840
ttcaaataat tttctcccga tttaatcatc tcaagatgag gttcacttct ttatttgaat   9900
ataccattat aaggaaatag atcatgcgcc ctcttgttta aaggaatttg atgttttttt   9960
atattcgctc tctttgagat atacctgtca tccagcagtg gtaaaaagga tagtatatag  10020
ctgacaaata tgttcatata atttccttgt gggtaatttt gatattctct ttctatctta  10080
atacgtgtta tgagcaccgg ctaatgaccg aatggggtat gaatggaaca ccggaggtcg  10140
aggcttttgg cagcctcttc gacgtctggc ccatgatcgg cgacgaaagc aaaagcaggg  10200
gatgagagag tagagaattg gagacgagac tatagattga atcttgcttg gttcattcat  10260
gatttcgtgg cccttaatta ggcttacgat tgaactgaat tagctaataa aaaaggataa  10320
caaagtcttc tctaaatgta agcaatcgga tcactatcgc tcgtccggca tgccgcgtca  10380
gttttcagct cgcgtgatct ccttcgacgc cgcttggacc ggttgctgca tccgcgtagt  10440
tgcgtttctt catgtagacg attccgaccc tttacattac aactacttgg aattctttga  10500
gtgttctaaa ataatttgga tagtggtaca tatgtggtta cattttctta atggtgacat  10560
atagccaagt tggactaaga ttaattttaa tttgtgtgga atgagaaaga gtcaagacag  10620
tttgatacgt agaagtttgc atattcagaa ccttatactg gtttgtcttg gtttattttc  10680
ttgacaatgc agctttgaca gttcctcggt ccaaagagaa atgcgacaac actcccatgc  10740
cggtaaaaga tggcctgata tctgaagatg atgcaccggt acatctgcat cagaagcccc  10800
tgcaggcgac agccatggca gccatatgac tgacctgtaa tcctacaaga aaccaactga  10860
agattcatat gtggactgag tgaaattatg aaagttattg gaataaattg ttgctctgta  10920
tgtgagagca agcttcagtc cgttagcctg gttcctttta gtagtgttct actattggga  10980
gatcttcatc aacattttac atgaaacgtg atgtaatgaa cctctgttaa ttgttaattg  11040
tcagagctct agttttttgt ggtataaatt ttgttgcaag ggggcaatgc actcaacttt  11100
tgaatcattt gattggtatg gaaatcattg catttgtgca gagttcaggc agagttcagt  11160
tcttgcattt gcacatcgta ttactattac ctggccttgt ttggcacatc tccagttcca  11220
gctccacctc tcctagagct ggagctcagc caaacagttt cagctccacc gaaaatggga  11280
```

gcggagctgg gtggagcact ctaacaaaat gaactagaga ggtggagcta ggttaagctg 11340
ttccacaact ccacttcaga tctaactcct aaagttaaat ttaaaagttg aagctctacc 11400
aaacgagaaa acggacgata tgccactgta taggttgggt tcgaatgaaa tgccactcaa 11460
tacaatgtat cggataaaat gccactcaat acgttgccta ttggatgaaa tgccac 11516

<210> SEQ ID NO 4
<211> LENGTH: 11403
<212> TYPE: DNA
<213> ORGANISM: Oryza sativa

<400> SEQUENCE: 4
tctagatata ttacaggcct aaaattcgga tcacatattt aacacgtagt tgtgtagctg 60
tggtaccttc cgttcaggtc cagcagtggc tttccttgaa cgatactgta cactctagta 120
aaggacaaag aacacgtcaa agctggacac gagatcgaca actgcctgct ggcgggttct 180
tgcaagttgc atgtcggttg agttgtgatc atcgatctct cggaaggcgg agggaactat 240
gtctctctct ctctctctct ctctgtttct cgttagaact gaggtaacta tctcgaaata 300
atcatttctg aggctgcagt tgaagaagtt cagtagccac atctaatata tgctacattt 360
taatattata cgaatcttaa aaaaccttag tacgtgatgc aagaccgaat caatataaac 420
acagtgctgt gcgagcaaag aaccaggctc taccatatcg attggattgt gaaattcgag 480
acgtcgattt tcctctaatt tcaaacaaat ttgacacaaa tcgttcgcaa tacttgtgaa 540
agtcctttcc agtcagcaat tctttttttt taaaagttgt gggacccacc tgtcatactc 600
ctcccactct tcctccctct tactcttcct ctctctcttc tctctctcac tcttcccttc 660
tctctctcac aggcggcaga caggggacag agcagcgtcg gcagcagcgg caagcggcgg 720
caggggcagg tgacgcgaag tcggcagcgg caggggatga gggtgacgtg gacgaggatg 780
gtgatggagg agtggaggac gacgacgagg acgacgctcg ggcgctagca gcggcggcta 840
tggcggatag gcggcggcgc acgtcgaacg aacggcggcg gggacggacg gagcttaggg 900
tggcgggatg gcggcaggcg gtgtcggagg ctgctcgggg cgtcgagaga cagaggcggc 960
cggtggctga ggggtgggga tggcggtgag gagaggagga ctcttcctct gccaccgcgc 1020
tcgccccctc cgccgctcgc ctcgtcggcg cgctagcctg ctccaacgcc ggtagacacc 1080
aagccgccgc tcgagcccgt cccctgcgcc gtccttcctc gccgccgcgc ttgcctcgca 1140
cgcagccaga tgcagacggc aacgcgctag cgcatgggga tggcggcgcg gagcatggtg 1200
tcctccttgg ccatgacggc gacgttgacg cggaggccgt ctcggcggcc ccttcctcgg 1260
tagccacgac cgccgccgtg gcggccgaca tggcgaagct cccctccatc gtggtggctg 1320
acgcggcgaa gttcccctcc ttcctcgccg ccgtcactcc atgtccccccg cctgccacag 1380 acctacagtg cgtgttcaga gagtgaaaga agagagagag gaatagtgga ataggagtat 1440
gacaggtggg ctccacattt ttttaataaa taaaatattg gctggactgc cacgcgtacg 1500
ccacgtagac caaaaccgcc gcggattggg tcgaggggat aattcgtcct gtttgcatag 1560
ttgggtgtaa agaatgtccg gttttgtggt tcagggggta attcgaacga ccgcgatagt 1620
tgggagggta attcgtactt tttcctattt tttatctaat aaaaattaac ctataataaa 1680
ataattagtg atcaaatgtt taaagattta gaatcttaaa attcgtgctt attgagtggg 1740
acggagggag tatttttgtt gcaatataca ttaataaata tatgatttta ttaagatatt 1800
tttaggacta taagataaat gttttagtga attcaattta gtacatccat ctactagctc 1860
cacataatct ataatcaatt taataaacaa tttatacaat aattacatat aaactaccct 1920

-continued attaatatat aatcccacct atcatacgcg cgttgtgtct tagagtccgt gctacagctg 1980
gctacaaatt tgtagcccgc tgctcctctc tctcttttat cttctcggca tatgtttata 2040
gctagattat aggttttgtt tggtttattg gactaatcca ttagtccctc cattttagtc 2100
ccttttattt tttaagaatt ggaggtactt atagtttata gttataggga ctaaattggt 2160
agctcatctc ttctctcttg gtccacgtgc ctttagtccc ttttagtctc tggatctaaa 2220
cagtatggga ctaaagtttc cagtacaggg tcatagcggt tatagcttgt tattgtaccc 2280
tctaagattt aaagtttgac tatagcttta tagctttagg cctgatttag tttcccaaat 2340
tttttaccga aaatatcaca ttgaatcttt ggacacatgc atagagtgtt aaatatagtt 2400
taaaaaaact aattgcataa ttagagagga atcgcgagac gaatcttttg agcctaatta 2460
gtccatgatt agccataagt gccatagtag cttagatata ctaatgacga attaattagg 2520
ctcaaaagat tcatctcgcg gttttcaggc aatttatgaa attagttttt tcattcatgt 2580
caaaaacccg tcgtgatatc cggtcaaaca tccaatatga caaaaaaaaa ttcttttcgc 2640
taaggctctt atgtaaaacg aacaacacgg tactccctct gtctaaaaaa aaaggcaaac 2700
cacgggtttg cgtgccaacg tttgactgtc cgtcttatat gaaatttttt tataattagt 2760
attttcatta ttgctagatg ataaaacatg atgaatattt tatgcgtgac ttatcttttt 2820
aatttttttc ataatttttt caaataaaac gaatggtcaa atgttagaca cggaaatcgg 2880
gttttttttt ttagacggag ggagtaggta ggagtaccag taataaaaac gaagaatacg 2940
cgttatagat ttctccacgg agggagaagc gaataaaatc ccccgcagca tatggcgtga 3000
cgaattgacg atatacaaat ttccacgggg accagtcttc ctcaatcctc tgccttgcat 3060
cttctccatc cagcgataca ataccagaag tccaaaaaac caccggtgcc gtatggccac 3120
agccggcgct gccgttgacc ggcttctacg ccgtctggcc tccggtgctg gccgtctgga 3180
gctgccctcg agcatagacg aggacatggc gcatgtaaag cgaaccctgg cgaggttgca 3240
agatgtgctg ctaaccgtag aagggaaata cttcaagatg ggcgcggagg tgcaggaatg 3300
gatgaggaag atcaagcaga ttgcttacgg cattcaagat ttgctggatg agtttgagga 3360
cagtagcggc accggatccc aaaggaacgg ctccaggatt tcagaggttc ggcttcggca 3420
catccattta tggaggggac aattagaatt accaacttgt cttttctcat tccaaatcag 3480
cattttctca aggaaaaact gttttcttta ataaaaaaaa aggggaaaat gggttctttt 3540
agtgaagtat ttcttatgcc agtgtccttg gatgccacaa taatcttttt gtagttctgt 3600
aaaaatatga tgattatata tttgtaaatg cccttcgagt gaccatttta gattattatt 3660
tgcagggaac gctatcgtgt tcgtcagctc cattttttctg ccatcttagt agatcacaaa 3720
gaataagggt actgaaaaga aagttagatc aatcaacaaa agatacttct gtatttagtt 3780
tactgcagca cagcttatcc aatcttgaca aatccaatga gcaagaagtt ctgttacata 3840
gaactgaaat cattggaagg gatactgaca aagaaaatat aaaaaatcta ttgttacaaa 3900
atgatgtgga taaattaccc atcattccga tagttggcct tgcggggctg ggaaaaacgg 3960
ctgtagcaaa attgattttc catgaacagg gagaagggtg gaattttgat cagcgcatat 4020
gggtccattt ggacaagaaa ttggatctta acaaaattgc taacagtatt atctcacaag 4080
ttaaccaatc agtagatacc acaaagaatc aaattcagaa caacttacag tttaaaagga 4140
attgtcttca agaagttctt tgtgaccaaa gcagtttgat agtattggat gacttattta 4200
gcacagagga aaaccagatt gcagagttga aggaaatgtt gaggggtaca aagaagggaa 4260
ccaagatcat tgtgactact tccagtgaaa tatctgcaga gctaatacac acagttccac 4320

-continued

```
catacaagtt gggcccttta tctgaaggtg actgttcaac aatattttgt caaagagcat   4380
ttggtgatgg acatgaaaac agcagcctca ctgaaattgc gaagcaaatt gtgaaaaggt   4440
gtgaaggcat accggctgta gcttattctc ttggttcatt ggttcgtaac aagaataagg   4500
aggcctggtt atatgcaaga gacaaagaaa tatgggaatt accaacatta tttcctaatg   4560
ggtttgaatt acttgcatcg ttcagtgaaa tgtatatatg tatgccctcg gctttaaaat   4620
catgctttgc atacttatca accataccca aaggaacaat aattgatagg gagaaactta   4680
ttgaacagtg gatagcactt gacatggttg ggtcgaagca tgggacctta cctgcttatg   4740
tgcaaggaga gatgttcatc cagcaacttc tatcgatatc ttttcttcaa gtccgaaaca   4800
agccctctgt aagttgctca atatattgag ccaaaacctt ggctatgttt cgagatagtg   4860
ctaatataaa ttggcatgaa tagtaataat atatttttct gtcccttaaa atagtttttt   4920
ttttctatta ctgtcattca tgtgactcat tttgtttttt agtatgataa aatgctatat   4980
attctcaaaa gacaagaaaa actatatatt gttcataaat atttgttttt tttctgtgat   5040
atatctgcct gagtcttgag gtatatatgt cggctaagat agaaagttgg agctgaatag   5100
ctgatacagc gtgaaataag ggaggtagaa agcagaagct ggtataaatg tactattgat   5160
ttctagccat taactgtacc acgaaaagaa aattcatcat atataatgga ctcagtgatg   5220
ttgttcactg tgtatatttc ttttggatta cacatttcat gcatggtttt gtgggattat   5280
acaaaatcgc aagactgata agtaacccaa attcgaacaa ggtggttggt ttgaagcaaa   5340
tcaatgtgta acaaagtttt tctttttttca ggccaccaga atcagagaca ccaatcaatc   5400
taaggaactc cgtatccata acttggtcca tgactttgca atgtatgttg cccgtgatga   5460
tctcataatt ctggatggtg gagagaaggc cagtagcctt agaaaaaaca tccatgtctt   5520
ctatggagtt gtgaacaatg atattggaca atcagcactc cggaaaggtc tgctcagcag   5580
tgcaagggca gtacacttca agaactgtaa gtcagaaaag cttcttgtag aggcattctc   5640
agtactgaat catttgcgtg tcttggatct tagtggttgt tgtattgtag aattaccgga   5700
tttcattacc aatttgaggc atctgagata cctggatgtt tcatattcaa ggattctgtc   5760
attgtcaacc cagctaacta gtttgagtaa tctggaggta ttggatcttt cagaaacttc   5820
tcttgagttg ttaccatctt caattggctc atttgaaaaa ttaaaatact tgaatctaca   5880
aggatgtgat aaacttgtaa acttgccccc atttgtctgt gatctcaaga ggctagagaa   5940
tctcaaccta tcatactgtt atggaatcac tatgctaccc ccaaatctat ggaaacttca   6000
tgaacttcga attttggacc tctctagttg cacagatctt caagaaatgc catatttatt   6060
tggtaactta gcaagcttag aaaatctaaa catgtcgaaa tgctccaagc ttgaacaact   6120
accagaatct cttggtgatc tttgttacct acgatccttt aacctatcag gttgttctgg   6180
gcttaagatg ctgccagaat ctctgaaaaa tcttacaaat ttagagtata ttaatttgtc   6240
aaatattggg gagagtatcg atttcaatca gatacaacaa ctacggcaca ttctcaagaa   6300
aacatttttt tctggagata ttggagggag tgaactccaa acatgtgaac acgctgctga   6360
ttctgcagac agtaagaagg taatcttatc acatacatgg ttctgcaact aaacagaatg   6420
tagtgtaggt tttttctgtt tttttctttt tgatattttg attttgtgac tgatctactg   6480
tgtatacttt taccaatcaa ccatgtccac actaaaatag gtacttcaaa ctccttcaga   6540
aaactgttta tgtaaagaga cctagaccaa aagaataaca tggtttaagt ttctctgcag   6600
atcacatcat ccatgcatgc agaacatatg aaatgatctg acttgtcata gtgatatcta   6660
ggcaaaatac atcttttcaa aatatcacgt gtttcatggt tatagttgca aaagaccatc   6720
```

-continued

```
tttctaattt gcctagcttt cactaacatg aattattttg cagaagacac ttttcgtttt   6780
tatttcaatt tgcctgctat cactatcatg aattattttg catatattga tttaaagctt   6840
ttttttttt gccaacatac aactagagaa cataattaca tgtaaaagat attgaagagg   6900
cagtatttag attgtcatgt acttgtttgg tatttattga ggaataataa taaaaaatgt   6960
tggttaattt gaggtacttt tttattcgag atttgaggta ttttttaatt cattatttcc   7020
atctctactc taacttagat ttcatgaaaa ttattttcag gaaattacaa tggatttttc   7080
tgcaaatttg catggaaata ttactttgcc acccaagtgc tcaactggta catttgcttg   7140
agttgtttat ataaacaatt tttctttcga tacatttttc ataataaata tacgaaattg   7200
cattcaagtc gtgtaatttg tctattaatt ttgtgccacc aaggaataat gaatattttg   7260
aaacttccta tgttaattta gttgagtgtt tttattgtgt tctagtcctc atggagctct   7320
ttgggcatgt tccatgaatt tatagatgta tcatcatata aataatatga ctgcaatccc   7380
tttattgcat aatatagtct ggaactaagc ttaggttgtg tttttacttg aagttgggaa   7440
ctaatccctc tctatcacaa aacaaaacga ctcattagca catgattaat taagtattag   7500
atattttttt tgaaaaatag attaatataa tttattaaag caactttcgt atagaatttt   7560
tttgcaaaaa aaaaacacat catatagtaa tttgaaaaac gttttcacag aaaacgaggg   7620
agatgagtcg ggatcttcca ccaaagaact cagccttgta aattttgtta tataatattg   7680
tattctttgc aaacatcgta tcatatcagt gctctccata tcctttatat atatataaaa   7740
tgtagtgaaa tatgttgttt cataacataa atccattgcg gactatcttt gatactacct   7800
ccgtttcagg ttataagacg ttttgacttt agttaaagtc aaactactct aactttgact   7860
aactgtatag aaaaaatagt aatatttaca acaccagcat agtttcatta aatctataat   7920
tgaataaatt ttcataatat attagtcttg ggttaaaaat atgactactt ttttctacaa   7980
aattagttaa acttagagtt gtttgacttt gacaaaagtc aaaacgtcta taccctgaac   8040
cggaggggag tattagagtt gatgagaaga ttaaaaataa aggggtcaca tagtaccact   8100
agtcttaatg ggggtttaca tacacacatt atgcgaacta tataccatta tatctacaca   8160
cacacacaca caaacacaaa agaagttttt atctccaact tcttttttttt tttgcgggga   8220
aaggaaatat attattagaa tttactaact gtagcccata cagaaaatca ttattctgta   8280
attacgtacc gatgtgcaaa ttctaataaa tatctataca tcttcttttg caactagcag   8340
aagagaaatc tggtgaaaac tctgaacgat tcctatcagc tgcagttagg gaggattcaa   8400
gcagcactga tgtttctaca tatgtcaagc cggtggtgtc ctcacttatt ggagtgctgc   8460
gcagaccgac taggttggat gtgccagctg gcgcgatggc ttctcaggtt ggcctggccc   8520
agatgccatc tagcaacaat ggtaaggctg gaccgcatcc aacaatggct gcagctcaga   8580
ccccggagat tgatcaacct gtgcataaaa gggtccggtg ggatgatata atagactact   8640
cccgtcctcc caactcaaaa cctgccagga gtgcatctct tgtgcagtcg accgatctgt   8700
cgacaccaaa gaaaagttat aaaaaaattc actcaatgcc ggtggtctat tcgtcaattc   8760
caaaagggag ttccggagga acatacttga tgccagcaaa ggctatcgct tcttcctaca   8820
ggaggtatag cccacagaga tgggaacagc acattggtta tcaaggaacg gtgcgttcat   8880
tgtaattatt ccagaatata tatatgtgac ttgatatata tctccatttg attggaacac   8940
aggagtaata tatagctggt tttgcatttc ttacctggcc aggatgaaga tgaactgatg   9000
gtcgtgccac catttggtga gtgggatcag tcccccacat tacgaaaatc tgactttcgg   9060
tatgagaagg tcttcgctaa actcaccgaa gagaagatgt ctggtcaaag gcagaaaccg   9120
```

-continued

```
caacaggtat gaacaaactg ccaccaaaca gaacgtaaat aggcatgctc tgctgtttgc   9180
cagaattaaa tttcattgac tgctattgaa catatatata cttagtgcta atcaccaatt   9240
tgtgacatat aaaggtctca actatcaata aaaaaatcat gcaggctaac aataccaaaa   9300
aaaaaggaga aaaaatgaaa aaaaaattgg taaccaaaat tatagaggct gacattatca   9360
gttctcacca atcagtgatc ttgaaagaca caaaaccagt gccggagctt catggagatc   9420
aaagtgggtt ctggccccct ccaactccat gcaaattata ctatatgtat gtttatgttc   9480
ataaatacta ttcattagcc atctttcacg ttgattgaca taaaactcat gttaatggcc   9540
ccctcttaat agtttgtgaa gctgcgcata aaatcatctt gacaaatttt tggtaacaac   9600
tgggaagtgc taattatcaa tactgaacgt tctgaacaaa tcaaccattt atagacaatg   9660
caagagcaaa aaagaaatta gtatacccac aatatatttt gttgtaccct atctgagatt   9720
ctaggttgtc tattgtgaat ctgtttgtta ccaatcagtg aaatttagtc gtcctaaaca   9780
tcaaataaat ttataaattt ataaaaaata atttatgaac tggggaagta tatgttcaat   9840
tactctgcaa cgttatatat tgttatacta taaaatcacc atgatcaatg gcaataccct   9900
tctcttcttc cccagataac ttggtaactt taatatgttt attcttggct ttttttcgac   9960
aatactccct ccgtcccccc aaaaaaaaaa actcaattcc ttggtttccg tatctaacgt  10020
ttgaccgtcc gtcttatttg aaaaaattat gaaaaaaatt aaaaagataa gtcatgcata  10080
aaatattatt catgttttat catctaacaa taataaaaat acaatttata aaaaaatttt  10140
atataagacg gatggtcaaa tgttagacgc agaaatccaa gaattgagtc tttttggga   10200
tggataatac aagggatttt gactttttag ttgtaatgtt tgaccactcg tcttattcaa  10260
aaaatttgtg caaatataaa aaacgaaaaa ttgtgcttaa agtattttgg ataataaagt  10320
aagccacaaa taaaataaat aatagttcta attttttta ataagacgaa tggtcaaaca   10380
gtgcaaacaa aaagtcaaaa tccctacatt atttttttg agacaaaaat ccctacatta   10440
taggacggag ggagtagcta gatatacaga gatctatcca tatctagact ttagagtcgt  10500
gcgtacgaac atacctttt cccgatggta atcgaattcg aatcgtagtc cagtacacta   10560
ctcctacctt tattttccgg tttcgcgggc ttcctttcca gtatcgggca tctacagggt  10620
ggtggtggtc agttactcac tcggtcagat cagggcgtct ctatttgctc cgtcatgaaa  10680
aaaaaattat atttttcttt gtgtgtgttt tctgatcagg tgacactgcg attgtcctct  10740
tgcagagaaa accacggaat gagcgatttg gcgcggtgtg gcatgccgaa ctcctgcaaa  10800
aaagatgaac taactcaacg aaggcagcga taacggcggc ggtcgctcac tctcctcaat  10860
aattgagcaa ccggcttccg ttgtttttt tttctcgtat ttttaataat tttattcttt   10920
tattgaaatg ggggttgggc acagcgcgcg atgtacttgt gcgccacaca cttgaatttg  10980
atcacggtcg atcttctatg tcggtacgag aatccacgga tgaagattaa atacaagcac  11040
gaaaaaaaag agagtattag ctaatgatta attaaatttt aattatttaa aacttgaaag  11100
atgtatttat ttgatatttt aaagcaactc tgtttttgca cgaaatatat cgtttagcag  11160
tttgaaaaac atactaacgg aaactaaggt agaatatgta tcttaatcag aaaaagaata  11220
gattttataa aaccttacat tttatggtgc tttgaaaaac cacacatatt ataactcgtg  11280
atacataact acaagtttat agtctaaatg tttcacaaga gcccaccttt atttaaattt  11340
ccattgattt cagcatatct gaaatgatat tttttataag tagtgaatag ttaaaccgat  11400
aac                                                                11403
```

<210> SEQ ID NO 5

-continued

<211> LENGTH: 3078
<212> TYPE: DNA
<213> ORGANISM: Oryza sativa

<400> SEQUENCE: 5
atggttggcg ccgagatgct tgtggccgcg gcggtgagcc aggtcgcccg gaagatcaac 60
gacatcgtgg gggtcgcgca gggcgaggtg aagctgtgct gcaatttcag cgacgatttg 120
gagggcatca aggataccct tgtgtacctg gaaaccttgc tgaaaaatgc ggagaataac 180
tccttcggaa gcgacagggc caacctgcgc cactggcttg gccagatcaa gtccctggct 240
tacgatatcg aagatatcgt tgatgggtac tactcttcca aggagcagtt cgatgggggc 300
agctatgcac agaaggggtc attattctgc tcgctatcca atccaatgct tctgaaaggt 360
agcatggttt ataagatgaa atccaagaga gagatgctac agcaaagcca acagttgccc 420
aatcagtatc atttcctttc atatatcaat tcagctgtgc attattttga ggagaagcaa 480
acaacatcat acagaaatac tgacattgca attgtcggga gggatgctga tttggatcat 540
ctcatggatc ttttaatgca aaacagcgct gaagagcttt gtattatacc catagttggg 600
cctgtaggtt ttggaaagac aagccttgca cagttagttt tcaatgatac aagaacagag 660
gtattcagct ttaggatatg ggttcatgtt tccatgggta atatcaacct tgaaaaaatt 720
gggagagata tagtttcaca aactacagaa aaaattgagg gaaatatgca gctgcagtca 780
atcaagaatg ctgttcagcg tgtgctaaat aaatatagtt gcttgatcat aatagacagc 840
ctttggggaa aggatgaaga agtgaatgaa ttgaagcaga tgttgcttac aggtagacac 900
acagaaagca agatcatagt gaccactcat agcaataaag tagctaagct gatttccacc 960
gttccactgt acaagttggc agctttatct gaggatgatt gtttaaaaat attctctcaa 1020
agggcaatga caggtccggg tgacccgttg ttcagggaat atggagaaga aatcgttaga 1080
aggtgtgaag gcacaccctt ggtagccaat ttctcggtt ctgtggtgaa tgctcaacga 1140
caaaggcgtg agatttggca agctgcaaag gatgaagaaa tgtggaagat agaggaagat 1200
tatccccaag acaaaatttc accactattt ccatcattca agataatata ttataatatg 1260
ccccatgagc taagattatg ctttgtatat tgttcaatct tccctaaagg aactgttata 1320
gaaaagaaga aacttattca gcaatggatt gcacttgaca tgattgagtc caaacatgga 1380
accttgccac ttgatgtaac tgcggagaaa tatattgatg aacttaaagc aatctatttc 1440
cttcaagttt tagagcggtc tcagaatgat gcagaaagat ccagtgcttc tgaggaaatg 1500
cttcgcatgc ataacttggc tcatgatctt gctagatcgg ttgctggtga agatatcctt 1560
gttattttag atgccgagaa tgagcgcaat gccagatatt gcaattaccg ttatgcacag 1620
gtgtctgctt ctagtttaga gtcaatcgat cgcaaggcat ggccttccaa ggcaaggtca 1680
ctaattttca agaatagtgg tgtggacttt gagcatgtca gtgaagttct ttcagtgaac 1740
aaatacctgc gtgttttgga tctcagtgga tgttgtgttc aagatattcc atctcctatc 1800
tttcagctga aacaattgag atacctcgac gtttcatctt tatctattac agcactccct 1860
ctgcaaatta gtagctttca taagttacaa atgttggatc tttcagaaac tgaactaaca 1920
gagttgccac cctttataag caacttaaaa ggactgaatt atttgaatct ccaaggttgc 1980
cagaaacttc aacgattgaa tagccttcat ttgttgcatg atctacatta cctaaacttg 2040
tcatgctgcc ctgaagttac tagttttcct gaatctattg aaaatctgac caaactccgt 2100
ttcttgaatc tttctggatg ctctaagctt tcaacattac ctatcagatt tttggaatca 2160
tttgctagcc tctgttcttt ggtagatctt aacttaagtg gctttgaatt ccaaatgttg 2220

-continued

```
cccgactttt ttggcaacat atattcactt cagtatttaa atctgtcaaa atgtttgaaa   2280

cttgaggtat taccacaatc ttttggccaa cttgcatatc tgaaaagcct aaatctttca   2340

tattgttctg atcttaaact gctggaatcc tttgaatgcc ttacctctct tcggtttttg   2400

aatctctcga actgctctag gcttgaatat ttgccatcat gctttgacaa gcttaataat   2460

ttagagtctc tgaatttatc acaatgtctt ggacttaaag cactacctga atcacttcaa   2520

aaccttaaaa atcttcagct tgatgtttct gggtgtcagg attgtatagt acaatccttt   2580

tctctaagta ccagaagttc ccagtcctgc caacggtcgg agaaagctga gcaggtcaga   2640

tcaagaaaca gtgaaatttc agagatcact tatgaggaac ctgctgagat tgaactttta   2700

aagaataatc caagtaaaga tttggcctcc atctcacacc taaatgagga tagaattgag   2760

gagcctgaag ttgtcactga gccaagtgca actagaggta tggtacaaca gattccagga   2820

aaccagctct catcgccttc atctcatctt tcttcctttg catcaagctc agcgccattt   2880

gcatcctcct cttcggacac ctcaacaagt gagcatccag tgcctaatga agaggcggca   2940

gctttgacag ttcctcggtc caaagagaaa tgcgacaaca ctcccatgcc ggtaaaagat   3000

ggcctgatat ctgaagatga tgcaccggta catctgcatc agaagcccct gcaggcgaca   3060

gccatggcag ccatatga                                                 3078
```

<210> SEQ ID NO 6
<211> LENGTH: 3192
<212> TYPE: DNA
<213> ORGANISM: Oryza sativa

<400> SEQUENCE: 6

```
atggccacag ccggcgctgc cgttgaccgg cttctacgcc gtctggcctc cggtgctggc     60

cgtctggagc tgccctcgag catagacgag gacatggcgc atgtaaagcg aaccctggcg    120

aggttgcaag atgtgctgct aaccgtagaa gggaaatact tcaagatggg cgcggaggtg    180

caggaatgga tgaggaagat caagcagatt gcttacggca ttcaagattt gctggatgag    240

tttgaggaca gtagcggcac cggatcccaa aggaacggct ccaggatttc agagggaacg    300

ctatcgtgtt cgtcagctcc atttttctgc catcttagta gatcacaaag aataagggta    360

ctgaaaagaa agttagatca atcaacaaaa gatacttctg tatttagttt actgcagcac    420

agcttatcca atcttgacaa atccaatgag caagaagttc tgttacatag aactgaaatc    480

attggaaggg atactgacaa agaaaatata aaaaatctat tgttacaaaa tgatgtggat    540

aaattaccca tcattccgat agttggcctt gcggggctgg gaaaaacggc tgtagcaaaa    600

ttgattttcc atgaacaggg agaagggtgg aattttgatc agcgcatatg ggtccatttg    660

gacaagaaat tggatcttaa caaaattgct aacagtatta tctcacaagt taaccaatca    720

gtagatacca caaagaatca aattcagaac aacttacagt ttaaaaggaa ttgtcttcaa    780

gaagttcttt gtgaccaaag cagtttgata gtattggatg acttatttag cacagaggaa    840

aaccagattg cagagttgaa ggaaatgttg aggggtacaa agaagggaac caagatcatt    900

gtgactactt ccagtgaaat atctgcagag ctaatacaca cagttccacc atacaagttg    960

ggccctttat ctgaaggtga ctgttcaaca atattttgtc aaagagcatt tggtgatgga   1020

catgaaaaca gcagcctcac tgaaattgcg aagcaaattg tgaaaaggtg tgaaggcata   1080

ccggctgtag cttattctct tggttcattg gttcgtaaca agaataagga ggcctggtta   1140

tatgcaagag acaaagaaat atgggaatta ccaacattat ttcctaatgg gtttgaatta   1200

cttgcatcgt tcagtgaaat gtatatatgt atgccctcgg ctttaaaatc atgctttgca   1260
```

-continued

```
tacttatcaa ccatacccaa aggaacaata attgataggg agaaacttat tgaacagtgg   1320

atagcacttg acatggttgg gtcgaagcat gggaccttac ctgcttatgt gcaaggagag   1380

atgttcatcc agcaacttct atcgatatct tttcttcaag tccgaaacaa gccctctgcc   1440

accagaatca gagacaccaa tcaatctaag gaactccgta tccataactt ggtccatgac   1500

tttgcaatgt atgttgcccg tgatgatctc ataattctgg atggtggaga gaaggccagt   1560

agccttagaa aaaacatcca tgtcttctat ggagttgtga acaatgatat tggacaatca   1620

gcactccgga aaggtctgct cagcagtgca agggcagtac acttcaagaa ctgtaagtca   1680

gaaaagcttc ttgtagaggc attctcagta ctgaatcatt tgcgtgtctt ggatcttagt   1740

ggttgttgta ttgtagaatt accggatttc attaccaatt tgaggcatct gagatacctg   1800

gatgtttcat attcaaggat tctgtcattg tcaacccagc taactagttt gagtaatctg   1860

gaggtattgg atctttcaga aacttctctt gagttgttac catcttcaat tggctcattt   1920

gaaaaattaa aatacttgaa tctacaagga tgtgataaac ttgtaaactt gcccccattt   1980

gtctgtgatc tcaagaggct agagaatctc aacctatcat actgttatgg aatcactatg   2040

ctacccccaa atctatggaa acttcatgaa cttcgaattt tggacctctc tagttgcaca   2100

gatcttcaag aaatgccata tttatttggt aacttagcaa gcttagaaaa tctaaacatg   2160

tcgaaatgct ccaagcttga acaactacca gaatctcttg gtgatctttg ttacctacga   2220

tcctttaacc tatcaggttg ttctgggctt aagatgctgc cagaatctct gaaaaatctt   2280

acaaatttag agtatattaa tttgtcaaat attggggaga gtatcgattt caatcagata   2340

caacaactac ggcacattct caagaaaaca tttttttctg gagatattgg agggagtgaa   2400

ctccaaacat gtgaacacgc tgctgattct gcagacagta agaaggaaat tacaatggat   2460

ttttctgcaa atttgcatgg aaatattact ttgccaccca agtgctcaac tgaagagaaa   2520

tctggtgaaa actctgaacg attcctatca gctgcagtta gggaggattc aagcagcact   2580

gatgtttcta catatgtcaa gccggtggtg tcctcactta ttggagtgct gcgcagaccg   2640

actaggttgg atgtgccagc tggcgcgatg gcttctcagg ttggcctggc ccagatgcca   2700

tctagcaaca atggtaaggc tggaccgcat ccaacaatgg ctgcagctca gaccccggag   2760

attgatcaac ctgtgcataa aagggtccgg tgggatgata taatagacta ctcccgtcct   2820

cccaactcaa aacctgccag gagtgcatct cttgtgcagt cgaccgatct gtcgacacca   2880

aagaaaagtt ataaaaaaat tcactcaatg ccggtggtct attcgtcaat tccaaaaggg   2940

agttccggag gaacatactt gatgccagca aaggctatcg cttcttccta caggaggtat   3000

agcccacaga gatgggaaca gcacattggt tatcaaggaa cggatgaaga tgaactgatg   3060

gtcgtgccac catttggtga gtgggatcag tcccccacat tacgaaaatc tgactttcgg   3120

tatgagaagg tcttcgctaa actcaccgaa gagaagatgt ctggtcaaag gcagaaaccg   3180

caacaggtat ga                                                        3192
```

<210> SEQ ID NO 7
<211> LENGTH: 24
<212> TYPE: DNA
<213> ORGANISM: Artificial Sequence
<220> FEATURE:
<223> OTHER INFORMATION: C1454 forward primer

<400> SEQUENCE: 7

```
gtattacctg aaatcctagt ggtg                                             24
```

<210> SEQ ID NO 8

-continued

<211> LENGTH: 24
<212> TYPE: DNA
<213> ORGANISM: Artificial Sequence
<220> FEATURE:
<223> OTHER INFORMATION: C1454 reverse primer

<400> SEQUENCE: 8
aggaactacg gtattacaag gatc 24

<210> SEQ ID NO 9
<211> LENGTH: 24
<212> TYPE: DNA
<213> ORGANISM: Artificial Sequence
<220> FEATURE:
<223> OTHER INFORMATION: JJ817 forward primer

<400> SEQUENCE: 9
gatatggttg aaaagctaat ctca 24

<210> SEQ ID NO 10
<211> LENGTH: 24
<212> TYPE: DNA
<213> ORGANISM: Artificial Sequence
<220> FEATURE:
<223> OTHER INFORMATION: JJ817 reverse primer

<400> SEQUENCE: 10
atcattgtcc ttcatattca gagt 24

<210> SEQ ID NO 11
<211> LENGTH: 24
<212> TYPE: DNA
<213> ORGANISM: Artificial Sequence
<220> FEATURE:
<223> OTHER INFORMATION: JJ803 forward primer

<400> SEQUENCE: 11
aagtgagcat ccagtgccta atga 24

<210> SEQ ID NO 12
<211> LENGTH: 24
<212> TYPE: DNA
<213> ORGANISM: Artificial Sequence
<220> FEATURE:
<223> OTHER INFORMATION: JJ803 reverse primer

<400> SEQUENCE: 12
agccggtgct cataacacgt atta 24

<210> SEQ ID NO 13
<211> LENGTH: 24
<212> TYPE: DNA
<213> ORGANISM: Artificial Sequence
<220> FEATURE:
<223> OTHER INFORMATION: Pi5-1 forward primer

<400> SEQUENCE: 13
tacaagttgg cagctttatc tgag 24

<210> SEQ ID NO 14
<211> LENGTH: 24
<212> TYPE: DNA
<213> ORGANISM: Artificial Sequence
<220> FEATURE:
<223> OTHER INFORMATION: Pi5-1 reverse primer

<400> SEQUENCE: 14

-continued tcagaagcac tggatctttc tgca 24

<210> SEQ ID NO 15
<211> LENGTH: 24
<212> TYPE: DNA
<213> ORGANISM: Artificial Sequence
<220> FEATURE:
<223> OTHER INFORMATION: Pi5-2 forward primer

<400> SEQUENCE: 15
agtgaactcc aaacatgtga acac 24

<210> SEQ ID NO 16
<211> LENGTH: 24
<212> TYPE: DNA
<213> ORGANISM: Artificial Sequence
<220> FEATURE:
<223> OTHER INFORMATION: Pi5-2 reverse primer

<400> SEQUENCE: 16
tcatacctgt tgcggtttct gcct 24

<210> SEQ ID NO 17
<211> LENGTH: 20
<212> TYPE: DNA
<213> ORGANISM: Artificial Sequence
<220> FEATURE:
<223> OTHER INFORMATION: Actin1 forward primer

<400> SEQUENCE: 17
ggaactggat aggtcaaggc 20

<210> SEQ ID NO 18
<211> LENGTH: 20
<212> TYPE: DNA
<213> ORGANISM: Artificial Sequence
<220> FEATURE:
<223> OTHER INFORMATION: Actin1 reverse primer

<400> SEQUENCE: 18
agtctcatgg atacccgcag 20

<210> SEQ ID NO 19
<211> LENGTH: 24
<212> TYPE: DNA
<213> ORGANISM: Artificial Sequence
<220> FEATURE:
<223> OTHER INFORMATION: PBZ1 forward primer

<400> SEQUENCE: 19
accatctaca ccatgaagct taac 24

<210> SEQ ID NO 20
<211> LENGTH: 24
<212> TYPE: DNA
<213> ORGANISM: Artificial Sequence
<220> FEATURE:
<223> OTHER INFORMATION: PBZ1 reverse primer

<400> SEQUENCE: 20
gtattcctct tcatcttagg cgta 24

<210> SEQ ID NO 21
<211> LENGTH: 24
<212> TYPE: DNA
<213> ORGANISM: Artificial Sequence
<220> FEATURE:

-continued

```
<223> OTHER INFORMATION: Forward primer

<400> SEQUENCE: 21

gtccaaagag aaatgcgaca acac                                            24


<210> SEQ ID NO 22
<211> LENGTH: 32
<212> TYPE: DNA
<213> ORGANISM: Artificial Sequence
<220> FEATURE:
<223> OTHER INFORMATION: Reverse primer

<400> SEQUENCE: 22

cgctcgaggt ggcatttcat ccaataggca ac                                   32


<210> SEQ ID NO 23
<211> LENGTH: 24
<212> TYPE: DNA
<213> ORGANISM: Artificial Sequence
<220> FEATURE:
<223> OTHER INFORMATION: Forward primer

<400> SEQUENCE: 23

ggatgatgtg atctgcagag aaac                                            24


<210> SEQ ID NO 24
<211> LENGTH: 24
<212> TYPE: DNA
<213> ORGANISM: Artificial Sequence
<220> FEATURE:
<223> OTHER INFORMATION: Reverse primer

<400> SEQUENCE: 24

cagcctcact gaaattgcga agca                                            24
```